US 7,399,293 B2

(12) United States Patent
Oyibo et al.

(10) Patent No.: US 7,399,293 B2
(45) Date of Patent: *Jul. 15, 2008

(54) SYRINGE ASSEMBLY HAVING DISABLING MECHANISM WITH TAMPER RESISTANCE FEATURES

(75) Inventors: Lola Oyibo, Edgewater, NJ (US); Robert Cipoletti, Pompton Plains, NJ (US); Aaron Barere, Hoboken, NJ (US); Richard Caizza, Vernon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/681,804

(22) Filed: Mar. 5, 2007

(65) Prior Publication Data

US 2008/0009796 A1 Jan. 10, 2008

Related U.S. Application Data

(63) Continuation-in-part of application No. 10/838,687, filed on May 4, 2004, now Pat. No. 7,331,934.

(60) Provisional application No. 60/523,490, filed on Nov. 20, 2003, provisional application No. 60/490,939, filed on Jul. 30, 2003.

(51) Int. Cl.
*A61M 5/00* (2006.01)
*A61M 5/315* (2006.01)

(52) U.S. Cl. ........................ 604/110; 604/228

(58) Field of Classification Search ............ 604/110, 604/181, 187, 198, 218, 223, 228, 241, 227
See application file for complete search history.

(56) References Cited

U.S. PATENT DOCUMENTS

| 3,478,937 | A | 11/1969 | Solowey |
| 4,367,738 | A | 1/1983 | Legendre et al. |
| 4,493,703 | A | 1/1985 | Butterfield |
| 4,699,614 | A | 10/1987 | Glazier |
| 4,731,068 | A | 3/1988 | Hesse |
| 4,775,363 | A | 10/1988 | Sandsdalen |
| 4,781,684 | A | 11/1988 | Trenner |
| 4,820,272 | A | 4/1989 | Palmer |
| 4,826,483 | A | 5/1989 | Molnar |
| 4,840,616 | A | 6/1989 | Banks |

(Continued)

FOREIGN PATENT DOCUMENTS

CN 2536246 Y 2/2003

(Continued)

*Primary Examiner*—Matthew F Desanto
(74) *Attorney, Agent, or Firm*—Jeanne P. Lukasavage

(57) ABSTRACT

A syringe assembly having passive disabling structure includes a barrel and a plunger rod assembly. The plunger rod assembly includes a plunger rod and a stopper connected by an indexing locking element. The number of strokes of the syringe plunger before the stopper is locked into the barrel rendering the syringe assembly unusable is determined by the number of detents on the plunger rod and stopper which engage the locking mechanism. Upon completion of the final delivery stroke, any attempt to withdraw the plunger rod from the barrel will cause the locking element to engage the barrel and trap the stopper in the barrel preventing further use of the syringe.

18 Claims, 46 Drawing Sheets

U.S. PATENT DOCUMENTS

| | | |
|---|---|---|
| 4,863,427 A | 9/1989 | Cocchi |
| 4,883,466 A | 11/1989 | Glazier |
| 4,908,020 A | 3/1990 | Pettersen |
| 4,915,692 A | 4/1990 | Verlier, Jr. |
| 4,923,443 A | 5/1990 | Greenwood et al. |
| 4,950,240 A | 8/1990 | Greenwood et al. |
| 4,961,728 A | 10/1990 | Kosinski |
| 4,973,308 A * | 11/1990 | Borras et al. ............... 604/110 |
| 4,973,309 A | 11/1990 | Sultan |
| 4,973,310 A | 11/1990 | Kosinski |
| 4,986,812 A | 1/1991 | Perler |
| 5,000,737 A | 3/1991 | Free et al. |
| 5,021,047 A | 6/1991 | Movern |
| 5,037,393 A | 8/1991 | Ellgass |
| 5,047,017 A | 9/1991 | Koska |
| 5,062,833 A | 11/1991 | Perler |
| 5,078,686 A | 1/1992 | Bates |
| 5,085,638 A | 2/1992 | Farbstein et al. |
| 5,085,640 A | 2/1992 | Gibbs |
| 5,090,962 A | 2/1992 | Landry et al. |
| 5,106,372 A | 4/1992 | Ranford |
| 5,120,314 A | 6/1992 | Greenwood |
| 5,149,323 A | 9/1992 | Colonna |
| 5,181,912 A | 1/1993 | Hammett |
| 5,183,466 A | 2/1993 | Movern |
| 5,195,975 A * | 3/1993 | Castagna ............... 604/110 |
| 5,205,825 A | 4/1993 | Allison et al. |
| 5,215,524 A | 6/1993 | Vallelunga et al. |
| 5,222,942 A | 6/1993 | Bader |
| 5,226,882 A | 7/1993 | Bates |
| 5,370,620 A | 12/1994 | Shonfeld |
| 5,432,757 A | 7/1995 | Chelminski |
| 5,531,691 A | 7/1996 | Schonfeld et al. |
| 5,562,623 A | 10/1996 | Shonfeld et al. |
| 5,593,386 A | 1/1997 | Helldin |
| 5,593,387 A | 1/1997 | Rupp |
| 5,624,406 A | 4/1997 | Labouze |
| 5,624,408 A | 4/1997 | Helldin |
| 5,643,211 A | 7/1997 | Sadowski et al. |
| 5,722,951 A * | 3/1998 | Marano ............... 604/110 |
| 5,833,660 A | 11/1998 | Nathan et al. |
| 5,928,202 A | 7/1999 | Linnebjerg |
| 5,989,219 A | 11/1999 | Villas et al. |
| 6,013,056 A | 1/2000 | Pettersen |
| 6,083,200 A | 7/2000 | Grimm et al. |
| 6,120,479 A | 9/2000 | Campbell et al. |
| 6,165,153 A | 12/2000 | Kashmer |
| 6,217,550 B1 | 4/2001 | Capes |
| 6,283,941 B1 | 9/2001 | Schoenfeld et al. |
| 6,361,525 B2 | 3/2002 | Capes et al. |
| 6,368,306 B1 | 4/2002 | Koska |
| 6,533,756 B2 | 3/2003 | Schoenfeld et al. |
| 6,599,269 B1 | 7/2003 | Lewandowski et al. |
| 6,702,784 B1 | 3/2004 | Sheckler et al. |
| 6,790,197 B2 | 9/2004 | Kosinski |
| 6,986,756 B2 | 1/2006 | Pelkey et al. |
| 6,991,618 B2 | 1/2006 | Lau et al. |
| 7,052,482 B2 | 5/2006 | Lau et al. |
| 2002/0173411 A1 | 11/2002 | Wallerstein |
| 2005/0187518 A1 | 8/2005 | Pelkey et al. |
| 2005/0199113 A1 | 9/2005 | Ku et al. |
| 2006/0079839 A1 | 4/2006 | Moh et al. |
| 2006/0079848 A1 | 4/2006 | Pelkey et al. |
| 2006/0167409 A1 | 7/2006 | Pelkey et al. |
| 2006/0178625 A1 | 8/2006 | Lim et al. |

FOREIGN PATENT DOCUMENTS

| | | |
|---|---|---|
| DE | 89 14 128 U | 1/1990 |
| FR | 2 646 087 A | 10/1990 |
| WO | WO 94/13336 A | 6/1994 |
| WO | WO/97/28836 | 8/1997 |

* cited by examiner ered leg of the locking element
US 7,399,293 B2

SYRINGE ASSEMBLY HAVING DISABLING MECHANISM WITH TAMPER RESISTANCE FEATURES

This application is a continuation-in-part of U.S. patent application Ser. No. 10/838,687 filed May 4, 2004 now U.S. Pat. No. 7,331,934 (US2005/0027250A1, published Feb. 3, 2005), which claims priority from U.S. Provisional Application No. 60/490,939, filed Jul. 30, 2003 and U.S. Provisional Application No. 60/523,490, filed Nov. 20, 2003.

BACKGROUND OF THE INVENTION

The present invention relates to syringe assemblies and particularly to syringe assemblies having an automatic disabling mechanism.

Throughout the world the multiple use of hypodermic syringe products which are intended for single-use only, is instrumental in drug abuse and in the transfer of contagious diseases. Intravenous drug users who routinely share and re-use syringes are a high-risk group with respect to the AIDS virus. Also, the effects of multiple use are a major concern in some countries where repeated use of syringe products during mass immunization programs may be responsible for the spread of many diseases. Re-use of single-use hypodermic syringe assemblies is also instrumental in the spread of drug abuse even in the absence of infection or disease.

Many attempts have been made to remedy this problem. Most notable are early contributions which relied on a specific act to destroy the syringe after use either by using a destructive device or providing a syringe assembly with frangible zones so that the syringe could be rendered inoperable by the application of force. Other attempts involve the inclusion of structure which would allow the destruction or defeating of the syringe function to a conscious act by the syringe user. Although many of these devices work quite well, they do require the specific intent of the user followed by the actual act to destroy or render the syringe inoperable. These devices are not effective with a user having the specific intent to re-use the hypodermic syringe. Accordingly, there was a need for a single-use hypodermic syringe which after use will become inoperable or incapable of further use automatically without any additional act on the part of the user. The automatic function is much harder to provide because the means for rendering the syringe inoperable must not prevent its filling or use under normal conditions.

A single-use syringe which automatically disables after injection is taught in U.S. Pat. No. 4,973,310 to Kosinski. This syringe contains a locking element positioned in the syringe barrel between the plunger rod and the inside surface of the barrel. In use, the syringe allows the user to draw a pre-selected amount of medication into the chamber of the barrel and deliver this medication, as through injection, into the patient. Any attempt to withdraw the plunger to use the syringe a second time will cause the locking element to embed itself into the inside surface of the syringe barrel to prevent proximal motion of the plunger rod.

There is still a need for a single-use syringe which will allow a pre-selected number of plunger rod strokes before the automatic disabling mechanism activates. For example, four strokes of the plunger may be required to complete the injection process. Such as when the syringe assembly is used to draw a diluent into the syringe barrel, dispense the diluent into a vial containing the substance to be reconstituted, drawing back the reconstituted medication into the syringe and then delivering the contents of the syringe into the patient.

SUMMARY OF THE INVENTION

An operable syringe assembly having a passive disabling structure includes a barrel having a cylindrical sidewall with an inside surface defining a chamber for retaining fluid, an open proximal end and a distal end including a distal wall having a passageway therethrough in fluid communication with the chamber. An elongate hollow plunger rod having a proximal end, an open distal end, and an interior surface is provided. A stopper has a circular-shaped sealing element having a peripheral surface forming a seal with the inside surface of the barrel and a boss member projecting proximally from the sealing element. A locking element interacts between the stopper and the plunger rod. The locking element includes a central body portion having at least one cantilevered leg extending distally outwardly from the body portion wherein the leg includes a sharp free end directed outwardly for engaging the inside surface of the barrel. The locking element is movably connected to the boss of the stopper and movably connected to the plunger rod interior surface. Structure for indexing the locking element distally in the plunger rod during proximal motion of the plunger rod to draw fluid into the chamber and for indexing the locking element distally on the boss of the stopper during distally-directed motion of the plunger rod for delivering fluid from the chamber through the passageway and means for engaging the locking element with the inside surface of the barrel sidewall for preventing reuse of the syringe assembly is provided.

Structure for engaging the locking element with the inside surface of the barrel sidewall may include an opening in the distal end of the plunger rod to shorten the axial length of the interior surface area of the opening for allowing the sharp free end to project outwardly past the plunger rod and onto the inside surface of the barrel.

The structure for indexing includes at least one detent on the interior surface of the distal end of the plunger rod, at least one boss detent on the boss and at least one cantilevered arm on the stopper having an outwardly extending rib near its free end sized to engage a recess in the inside surface of the plunger rod. The indexing structure further includes the locking element having at least one finger element extending inwardly from an aperture in the central body portion of the locking element. The locking element is positioned with its sharp free end contacting the interior surface of the plunger rod proximally of the at least one detent and the boss member is positioned in the aperture of the locking element wherein the at least one finger element is contacting the boss member proximally of the at least one boss detent and the outwardly extending rib is positioned in the recess of the plunger rod.

The syringe assembly may be configured so that the at least one detent in the plunger rod includes two axially-spaced detents and the at least one detent in the boss includes two axially-spaced boss detents so that the plunger rod can be moved distally one or two times before proximal motion of the plunger rod causes the locking element to engage the inside surface of the barrel, depending on the initial position of the locking element at the time of use. The two axially-spaced detents in the plunger rod may include two axially-spaced steps each having a blunt surface at its distal end extending inwardly from the interior surface of the plunger rod. The two axially-spaced boss detents may each include an inclined surface extending proximally inwardly and a blunt surface at a distal end of each of the inclined surfaces extending radially inwardly.

The at least one cantilevered leg of the locking element may include two cantilevered legs positioned on opposite sides of the central body portion. The stopper may further include two radial cam projections positioned to contact and force the two cantilevered legs outwardly when excessive proximally-directed force is applied to the plunger rod in an attempt to overcome the locking element's engagement to the inside surface of the barrel.

The at least one cantilevered arm of the stopper may include two cantilever arms positioned on opposite sides of the boss and said at least one recess in the inner surface of the plunger rod may include two recesses positioned on opposite sides of the plunger rod and configured to receive the outwardly extending ribs of the two cantilevered arms.

The syringe barrel may further include an elongate tip extending distally from the distal wall and having a passageway therethrough in fluid communication with the chamber of the syringe barrel. The syringe assembly may also include a needle cannula having a distal end, a proximal end and a lumen therethrough, wherein the proximal end of the needle cannula is connected to the distal end of the syringe barrel so that the lumen is in fluid communication with the passageway of the barrel. The syringe assembly may include a locking element made of sheet metal such as stainless steel. Further, the stopper and all its elements may be integrally formed of thermoplastic material.

An alternative operable syringe assembly of the present invention having passive disabling structure comprises a barrel including a cylindrical sidewall having an inside surface defining a chamber for retaining fluid, an open proximal end and a distal end including a distal wall having a passageway therethrough in fluid communication with the chamber. An elongate plunger rod having a proximal end, an open distal end, and a sidewall having an interior surface is provided. The interior surface includes at least one detent, and the sidewall has an axial opening and a positioning lug projecting into the axial opening. The lug includes a distal face and a proximal face. A stopper includes a sealing element having a peripheral surface forming a seal with the inside surface of the barrel and a boss member projecting proximally from the sealing element. The boss includes at least one detent on its surface. A retaining element is connected to the stopper by a frangible connection. The retaining element defines an axial recess having a proximal ledge for accepting the positioning lug of the plunger and for limiting the axial motion of the positioning lug in the axial recess. A locking element interacts between the stopper and the plunger rod. The locking element includes a central body portion having at least one cantilevered leg extending distally outwardly from the body portion wherein the leg includes a sharp-free end directed outwardly for engaging the inside surface of the barrel. A locking element is positioned with a sharp-free end contacting an interior surface of the plunger rod proximally of the at least one detent. The boss member is positioned in the aperture of the locking element wherein the at least one finger element is contacting the boss proximally of the at least one boss detent, so that applying proximally directed force to the plunger rod while holding the barrel causes the plunger rod to move proximally with respect to the stopper until the free end of the cantilevered leg moves distally along the inner surface of the plunger rod to said at least one detent and said proximal face of the positioning lug contacts the proximal ledge of the retaining element to move the stopper in a proximal direction for a distance selected by the user. Subsequently applying distally directed force to the plunger rod to discharge fluid from the chamber through the passageway causes the plunger rod to move in a distal direction along with the locking element, due to its engagement with the at least one detent, until the finger element of the locking element rides over the at least one boss detent and into contact with the at least one boss detent, and the plunger rod contacts the stopper to move the stopper distally to discharge fluid from the chamber. Subsequently applying a proximally directed force to the plunger rod causes the plunger rod to move proximally until the free end of the cantilevered leg moves distally along the interior surface of the plunger rod past the distal end of the plunger rod, so that the sharp end of both the at least one cantilevered leg engages the inside surface of the barrel to help prevent proximal movement of the stopper to render the syringe assembly unusable. The application of additional proximally-directed force to the plunger rod after the sharp end of the at least one cantilevered leg engages the inside surface of the barrel will cause the proximal face of the positioning lug to contact the proximal ledge of the retaining element with enough force to break the frangible connection on the retaining element and release the stopper from engagement with the plunger rod.

The syringe assembly of this embodiment preferably includes a flexible element connecting the positioning lug and the sidewall of the plunger rod for allowing the positioning lug to flex during assembly of the plunger rod with the stopper. The positioning lug and the flexible elements are preferably integrally formed of thermoplastic material.

The retaining element of the stopper may further include a proximally and inwardly directed ramp surface for flexing the positioning element outwardly during assembly of the syringe assembly. The syringe assembly may further include a radial projection or cam surface on the stopper positioned to engage and force the cantilevered leg outwardly when excessive proximally-directed force is applied to the plunger rod in an attempt to overcome the locking element's engagement with the inside surface of the barrel. By forcing the cantilevered legs outwardly, the radial projection or cam surface provides additional force for engaging the sharp-free end of the cantilevered leg into the interior surface of the barrel.

The plunger rod may be of two-piece construction comprising a distal portion and a proximal portion connected so that the tangential force required to rotate the proximal portion with respect to the distal portion is less than the axial force required to separate the proximal portion and the distal portion.

DETAILED DESCRIPTION OF THE INVENTION

Figure 1:
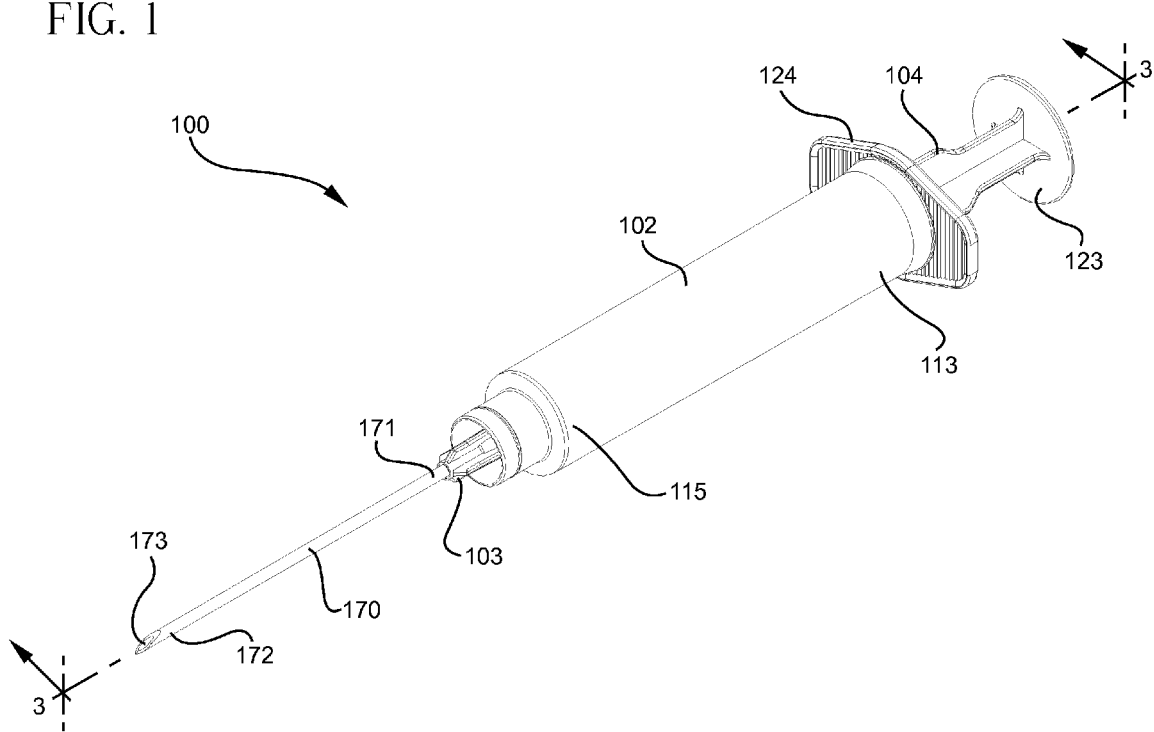
FIG. 1 is a side-elevational view of the syringe assembly of the present invention.
Figure 2:
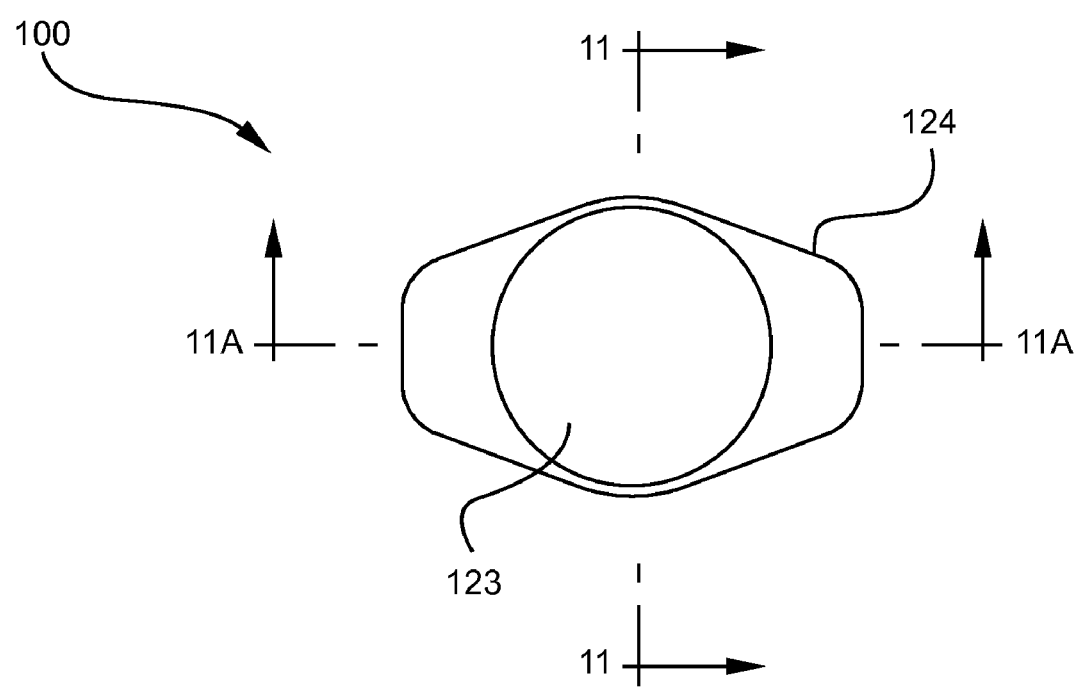
FIG. 2 is a side-elevational end view of the proximal end of the syringe assembly of FIG. 1.
Figure 3:
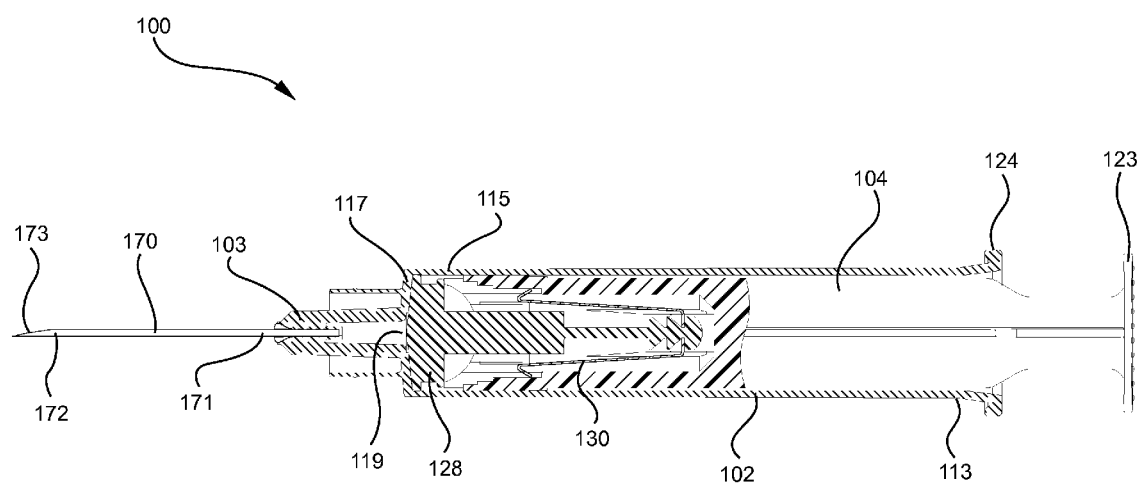
FIG. 3 is a cross-sectional view of the syringe assembly of FIG. 1 taken along line 3-3.
Figure 4:
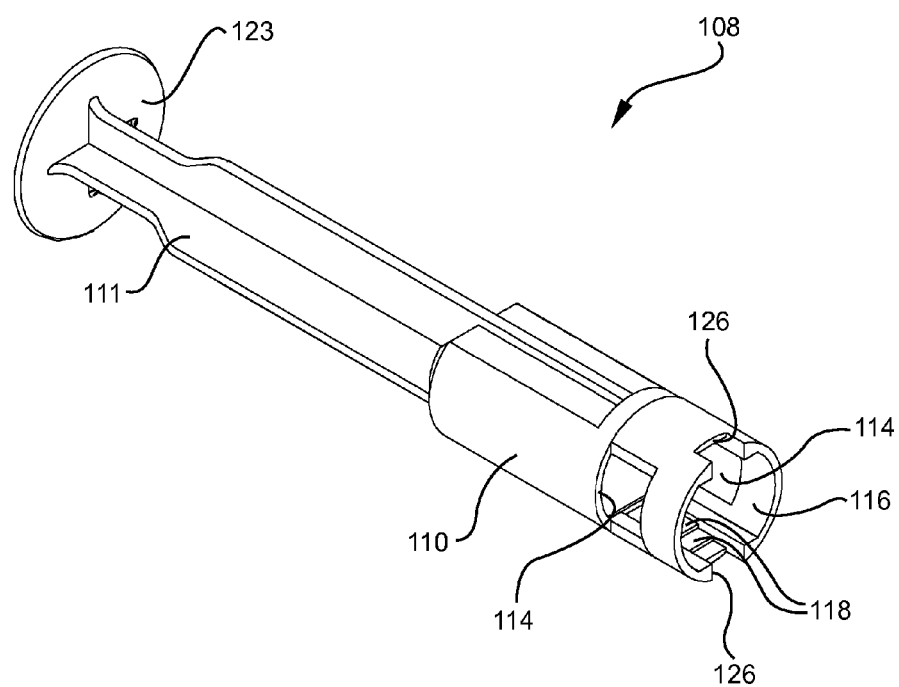
FIG. 4 is a perspective view of the plunger rod of the syringe assembly viewed from its distal end.
Figure 5:
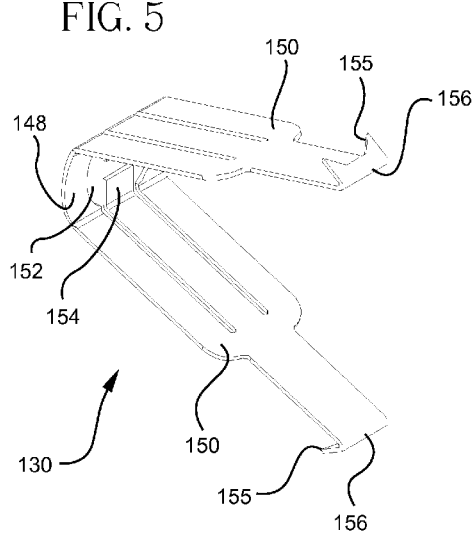
FIG. 5 is a perspective view of the locking element of the syringe assembly viewed from its distal end.
Figure 6:
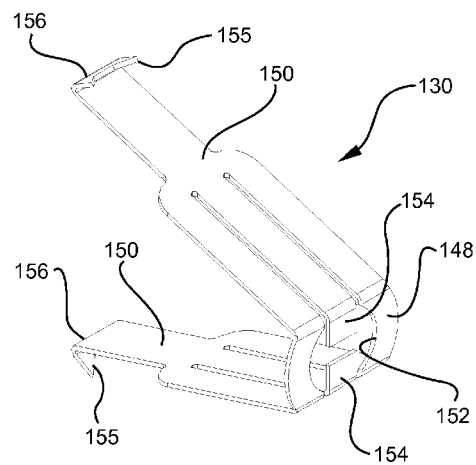
FIG. 6 is a perspective view of the locking clip viewed from its proximal end.
Figure 7:
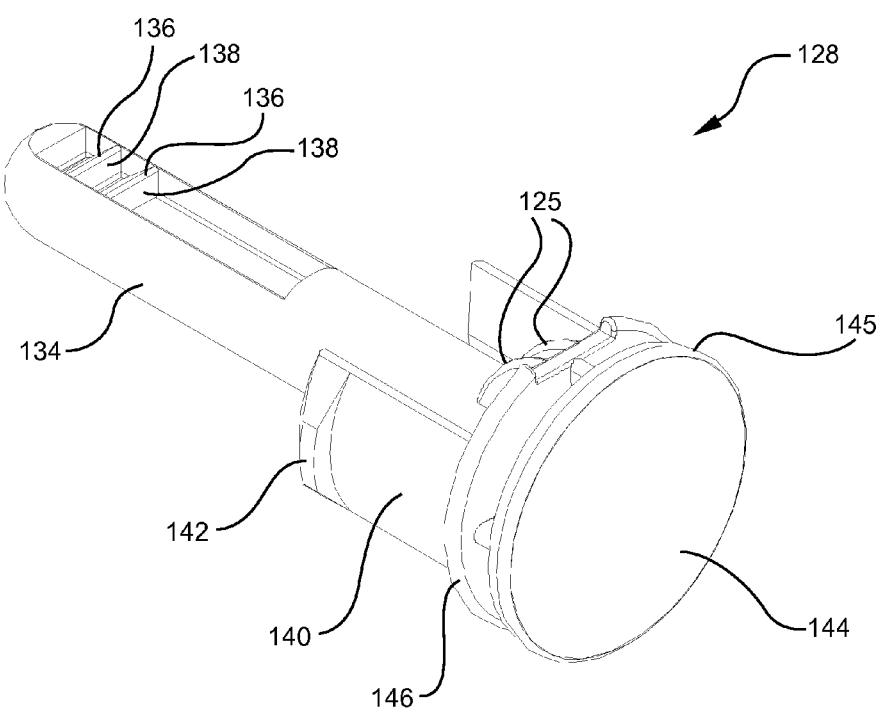
FIG. 7 is a perspective view of the stopper of the syringe assembly viewed from its distal end.
Figure 8:
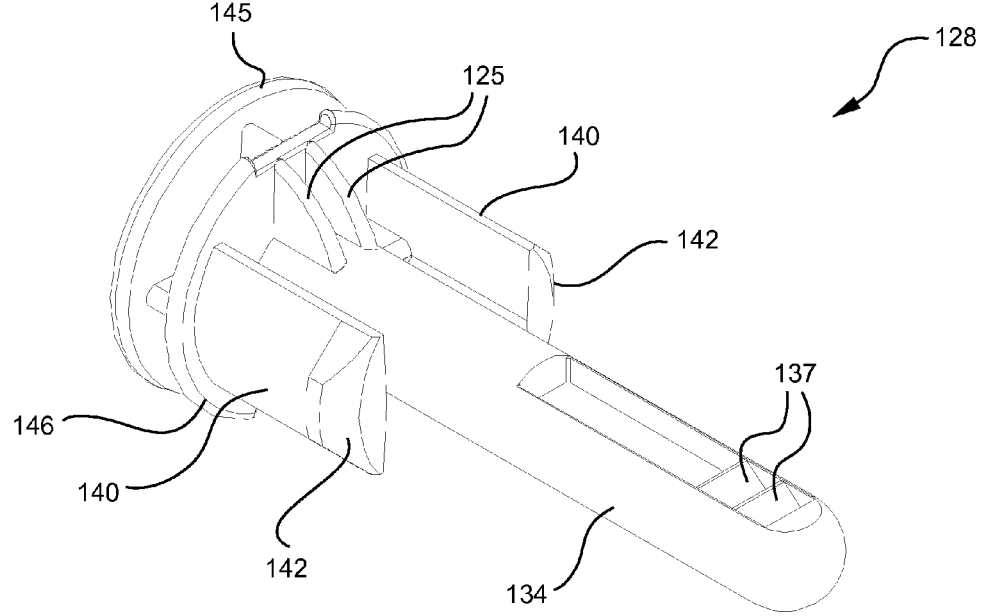
FIG. 8 is a perspective view of the stopper viewed from its proximal end.

The present invention is directed to a syringe assembly having a passive disabling mechanism. The disabling mechanism enables variable dosages by the syringe assembly and enables a selected number of cycles or strokes by the plunger rod before being automatically disabled. In one preferred embodiment, the disabling mechanism provides two aspirating and two dispensing cycles before being automatically disabled. The assembly enables the aspiration and dispensing of a selected volume of a diluent into a vial to reconstitute a drug, pharmaceutical agent, or other substance and then aspirating the reconstituted substance back into the syringe. A selected volume of the reconstituted substance can be injected or delivered to a patient where the volume of the substance that is delivered can be the same or different than the volume of the substance aspirated into the syringe barrel. The syringe is automatically disabled after the injection or delivery stroke by retracting the plunger rod, which activates the disabling mechanism.

The disabling mechanism is actuated by the axial movement of the plunger rod with respect to the syringe barrel and to the stopper, by moving the plunger rod in the aspirating direction. The stopper is coupled to the plunger rod to allow limited axial movement of the stopper with respect to the plunger rod. The disabling mechanism moves through a series of stages by reversing the direction of the axial movement of the plunger rod with respect to the stopper to move the mechanism in a step-wise manner to the disabling position. The disabling position of the mechanism is attained by the relative movement between the plunger rod and the stopper and is not dependent on the position of the stopper within the syringe barrel or the length of the stroke by the stopper. In this manner, the syringe assembly is able to dispense a desired volume of the drug or other substance, and the disabling mechanism can be actuated after the final dispensing or injection stroke regardless of the position of the stopper in the syringe barrel. By actuating the disabling mechanism, the stopper cannot be retracted to aspirate a substance into the syringe barrel but allows any substance remaining in the syringe barrel to be dispensed.

Referring to the drawings, a syringe assembly 100 having a disabling mechanism includes a syringe barrel 102 and a plunger assembly 104. Barrel 102 includes a cylindrical sidewall 106 having an inside surface 107 defining a chamber 109 for retaining fluid, an open proximal end 113 and a distal end 115 including a distal wall 117 having a passageway 119 therethrough in fluid communication with the chamber. In this embodiment, the distal wall of the barrel includes an elongate tip extending distally therefrom and having a passageway in fluid communication with the passageway in the distal wall. In this embodiment barrel 102 also includes a needle cannula 170 having a proximal end 171, a distal end 172 and a lumen 173 therethrough. The proximal end of the needle cannula is attached to elongate tip 103 so that the lumen of the needle cannula is in fluid communication with passageway 119 in the barrel.

Plunger assembly 104 includes an elongate hollow plunger rod 108, a stopper 128 and a locking element 130. Plunger rod 108 includes a proximal end 111, an open distal end 110 and an interior surface 116 and at least one aperture or recess 114 in the interior surface at the distal end of the plunger rod. The recess includes a distal face 121. In this embodiment, there are two recesses 114 having distal faces 121. The interior surface at the distal end of the plunger rod includes at least one detent. In this embodiment the at least one detent on the interior surface of the distal end of the plunger rod includes four axially spaced detents 118 with two detents on each side of the plunger rod. Each pair of detents is shaped to form axially spaced steps 120 with each step having a blunt surface 122 at its distal end extending inwardly from the interior surface of the plunger rod.

Stopper 128 includes a circularly-shaped sealing element 144 having a peripheral surface 145 forming a seal with the inside surface of the barrel. A boss member 134 extends proximally from the sealing element and includes at least one boss detent and in this embodiment, contains two boss detents 136. At least one cantilevered arm extends proximally from the sealing element and in this embodiment there are two cantilever arms 140 extending proximally from the sealing element. Each of the cantilevered arms includes an outwardly extending rib 142. The rib is sized to fit within recess 114 in the plunger rod. The axially spaced boss detents 136 each include an incline surface 137 extending proximally inwardly and a blunt surface 138 at the distal end of each of the inclined surfaces. The stopper is preferably integrally formed of thermoplastic material such as polyethylene. The circularly-shaped sealing element and/or the peripheral sealing surface thereon may be made of elastomeric materials such as thermoplastic elastomers, natural rubber, synthetic rubber and combinations thereof.

Locking element 130 includes a central body portion 148 having an aperture 152 therethrough and at least one cantilevered leg 150 extending distally outwardly from the body portion and at least one finger element 154 extending inwardly from the aperture. In this embodiment, at least two cantilevered legs with each of the cantilevered legs having a sharp free end 155 directed outwardly for engaging the inside surface of the barrel. The configuration of sharp free end 155 can be any configuration capable of engaging the inside surface of the barrel, such as a sharp edge or one or more pointed teeth and the like. The locking element may be made of a variety of materials, or combinations of materials, however, it is preferred to have the sharp free ends made of metal and it is also preferred that the entire locking element be made of integrally formed from sheet metal such as stainless steel.

Figure 9:
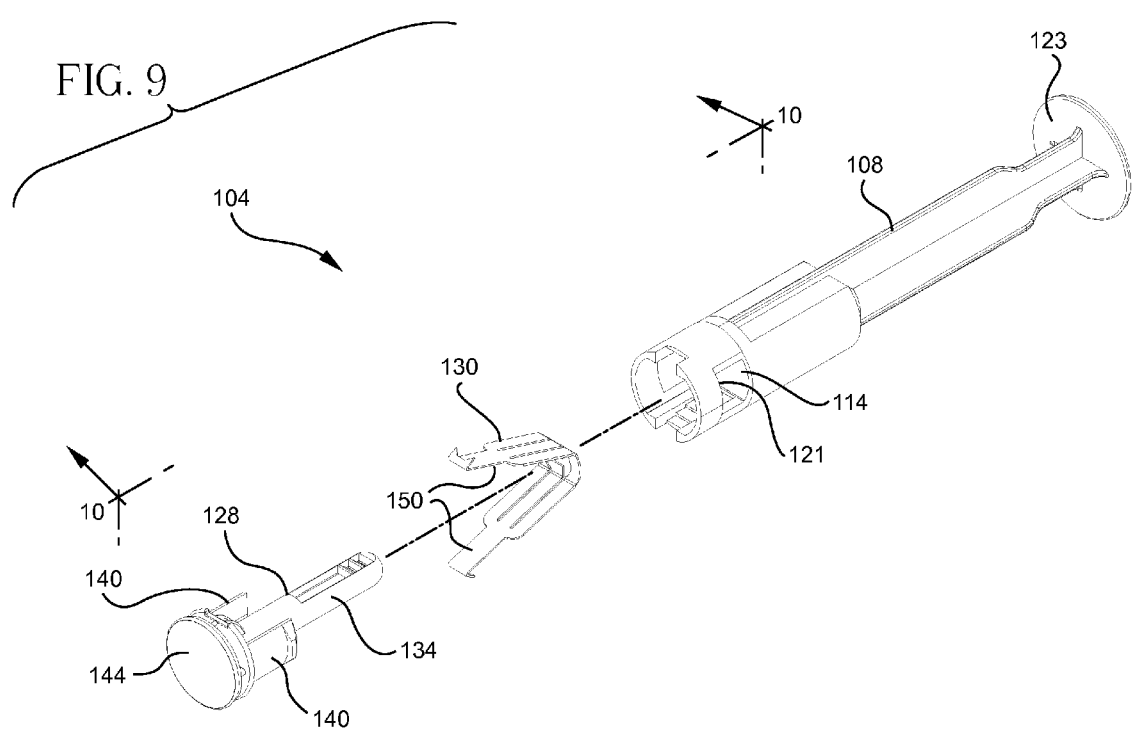
FIG. 9 is an exploded side-elevational view of the plunger assembly.
Figure 10:
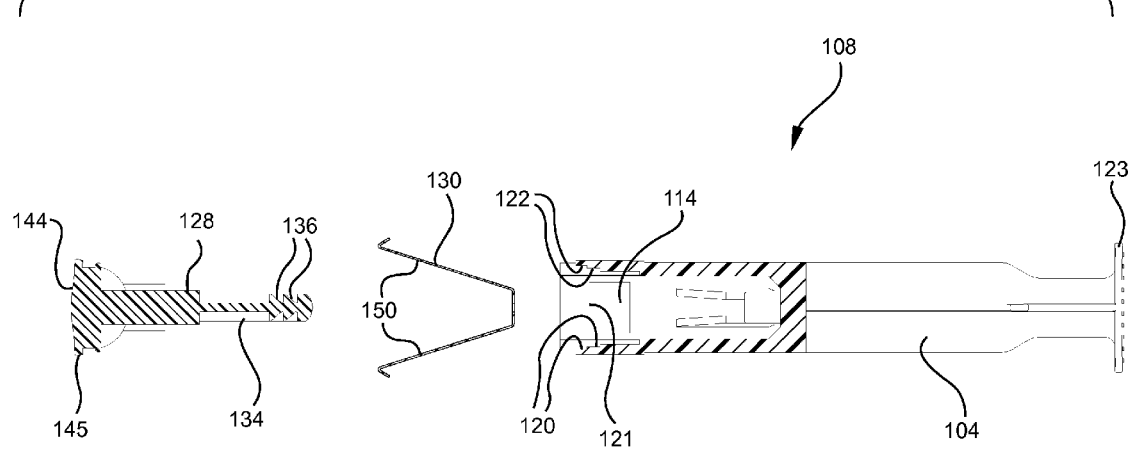
FIG. 10 is a cross-sectional view of the plunger assembly of FIG. 9 taken along line 10-10.

In this preferred embodiment plunger assembly 104 is assembled by inserting locking element 130 into the distal end of plunger rod 108. Boss 134 of stopper 128 is then inserted into the distal end of the plunger rod through aperture 152 of locking element 130 so that cantilevered legs 150 extend toward circularly-shaped sealing element 144 of the stopper as illustrated in FIGS. 9 and 10.

Figure 11:
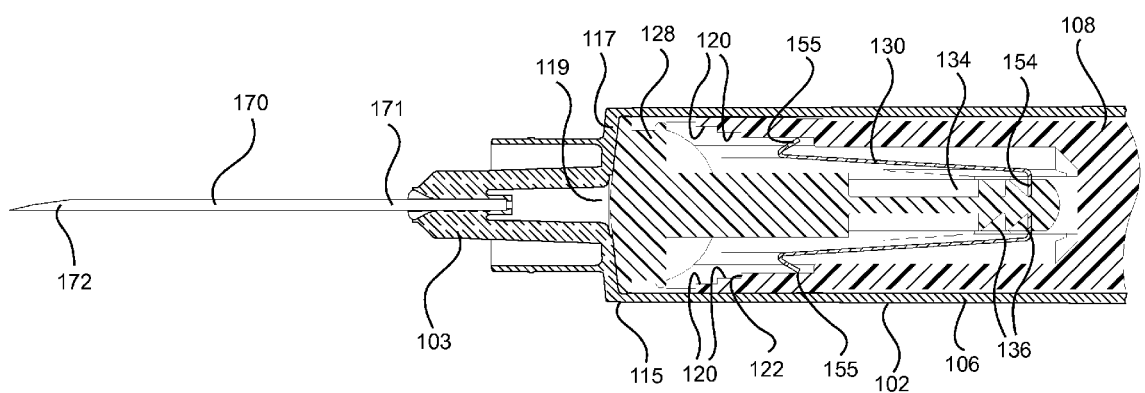
FIG. 11 is an enlarged partial cross-sectional view of the syringe assembly of FIG. 1 taken along line 3-3 showing the syringe assembly before use.
Figure 11A:
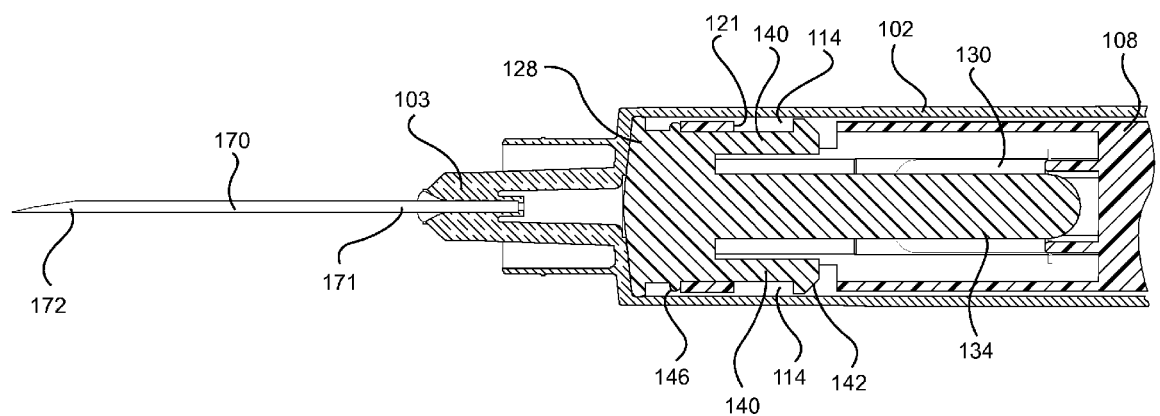
FIG. 11A is an enlarged partial cross-sectional view similar to FIG. 11 but rotated 90°.

As will be explained in more detail hereinafter, the plunger assembly is then inserted into barrel 102 through open proximal end 113 to the initial position illustrated in FIGS. 11 and 11A. In the initial position of the syringe element, locking element 130 is positioned with its sharp free ends 155 contacting the interior surface of the plunger rod proximally of axially spaced steps 120. Boss member 134 is positioned in aperture 152 of locking element 130 so that finger elements 154 contact boss member proximally of boss detents 136. Outwardly extending ribs 142 of cantilever arms 140 are positioned in recesses 114 in the plunger rod. Ribs 142 are configured to complement the recesses 114 for allowing limited axial movement of the stopper with respect to the plunger rod. The stopper 128 further includes stabilizing member 146 positioned proximally with respect to sealing element 144 and has an outer dimension complimenting the other dimension of the sealing element as shown in FIG. 11A, stabilizing member 146 has an outer dimension to contact the inner surface of the syringe barrel and is spaced from sealing element 144 to assist in stabilizing stopper 128 to maintain the stopper and boss member 134 in an orientation substantially parallel to the axis of the syringe barrel. In the position illustrated in FIGS. 11 and 11A, syringe assembly 100 is ready to use for drawing liquid into the chamber of the barrel.

As will now be shown, the operation of the plunger assembly of this embodiment includes a first aspiration stroke followed by a first dispensing stroke, a second aspiration stroke and a final dispensing stroke after which the syringe is disabled. The disabling elements prevent or inhibit movement of stopper 128 in a proximal aspirating direction thereby limiting the function of the syringe assembly to a single use. The maximum number of strokes being limited by a number of axially positioned detents in the plunger rod and the number of axially positioned boss detents on the stopper. However, the actual number of strokes the syringe may make will be determined by the position of the locking element with respect to the detents in the plunger rod and the detents on the stopper at the time of first use. For example, a syringe with two plunger detents and two stopper detents can be supplied to the end user as a syringe capable of two strokes or four strokes. This is an important feature of the present invention since a single syringe assembly can be provided with different stroke limitations before disabling.

Figure 12:
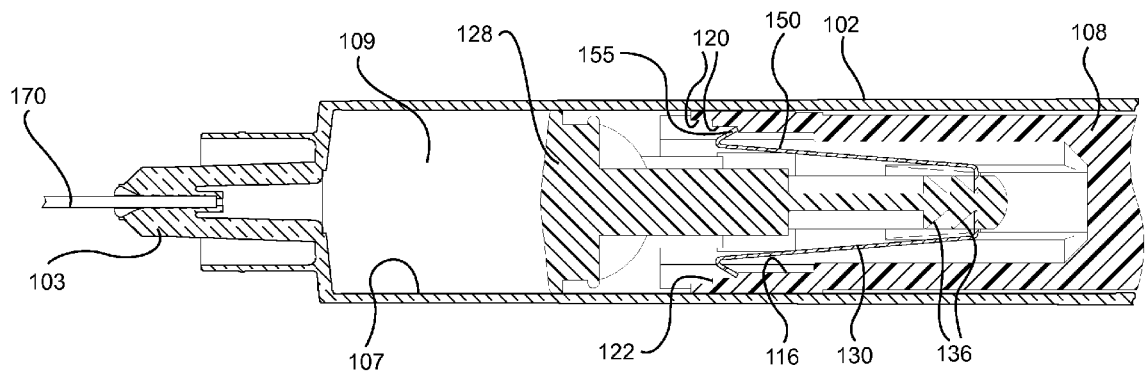
FIG. 12 is an enlarged partial cross-sectional view of the syringe assembly of FIG. 1 taken along line 3-3 showing the syringe assembly after a first aspiration stroke.
Figure 12A:
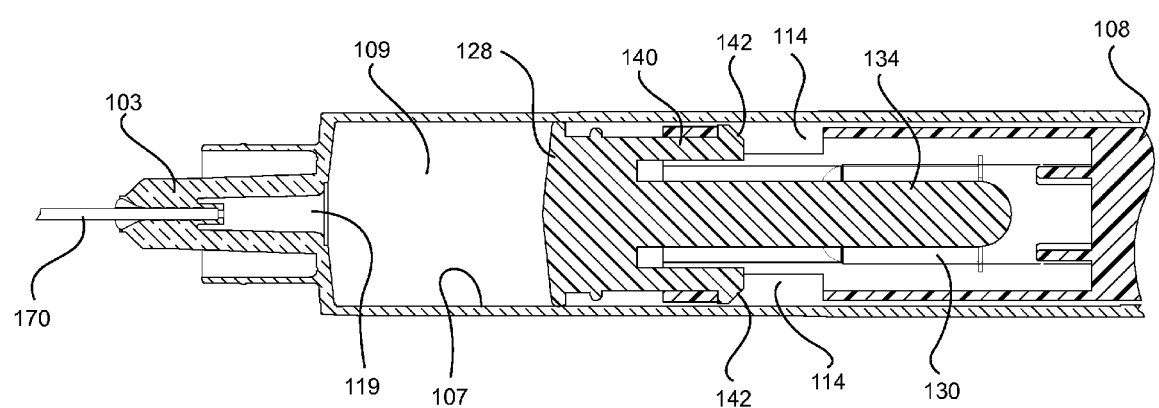
FIG. 12A is an enlarged partial cross-sectional view similar to FIG. 12 but rotated 90°.

The syringe assembly may now be used to draw liquid, such as a sterile water diluent into the chamber of the barrel by applying a proximally directed force to a thumb press 123 on the proximal end of the plunger rod while holding the syringe barrel. As illustrated in FIGS. 12 and 12A, this causes the plunger rod to move proximally with respect to the stopper until the free end of cantilevered legs 150 moves distally along inner surface 116 of the plunger rod and snaps past blunt surface 122 of the proximal most axially spaced steps 120, as best illustrated in FIG. 12. Also, during this first aspiration stroke outwardly extending ribs 142 engage distal surface 121 of the recesses 114 in the plunger rod as best illustrated in FIG. 12A. When ribs 142 engage distal surface 121 the stopper is drawn proximally with respect to the barrel as the plunger rod moves. The stopper is now moved proximally, through action of the plunger rod, until the desired volume of liquid is in the chamber as determined by the user.

Figure 13:
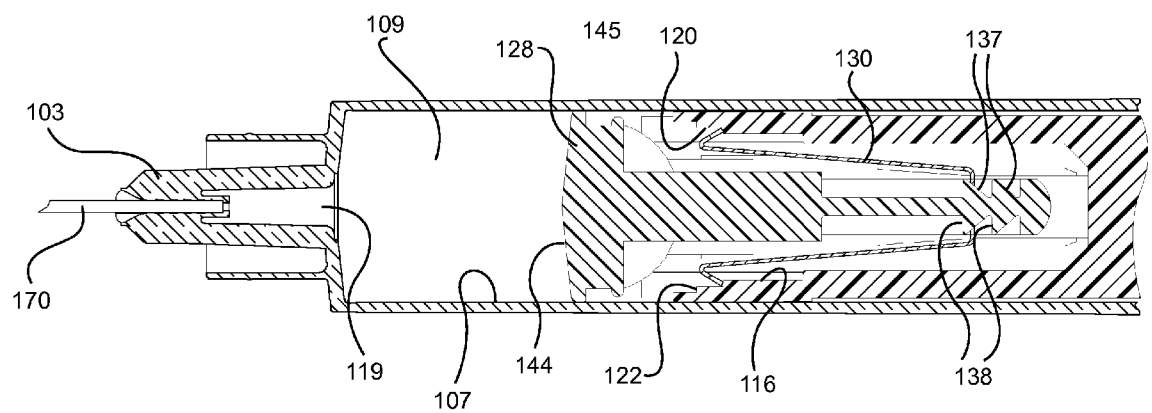
FIG. 13 is an enlarged partial cross-sectional view of the syringe assembly of FIG. 1 taken along line 3-3 showing the syringe assembly during a first dispensing stroke.
Figure 13A:
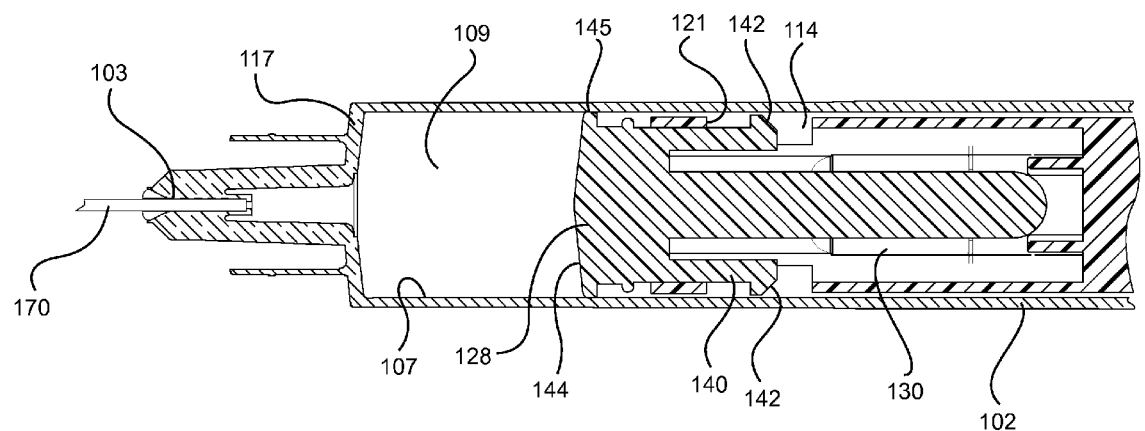
FIG. 13A is an enlarged partial cross-sectional view similar to FIG. 13 but rotated 90°.

The liquid diluent in the chamber may now be discharged into a vial of dry medication such as lyophilized medication, for reconstitution. This first dispensing stroke is accomplished by moving the plunger rod in a distal direction while holding the barrel. A barrel flange 124 is provided on the proximal end of the barrel to help control motion of the barrel during use of the syringe assembly. As best illustrated in FIGS. 13 and 13A, as the plunger rod moves distally, locking element 130 moves with the plunger rod dragging the locking element with it so that finger elements 154 on the locking element slide from the proximal most to the distal most boss detent by riding up inclined surface 137 and falling into the second detent. When the plunger rod contacts the stopper, the stopper will begin moving in a distal direction along with the plunger rod to discharge liquid diluent from the chamber into, for example, a vial of lyophilized medication.

Figure 14:
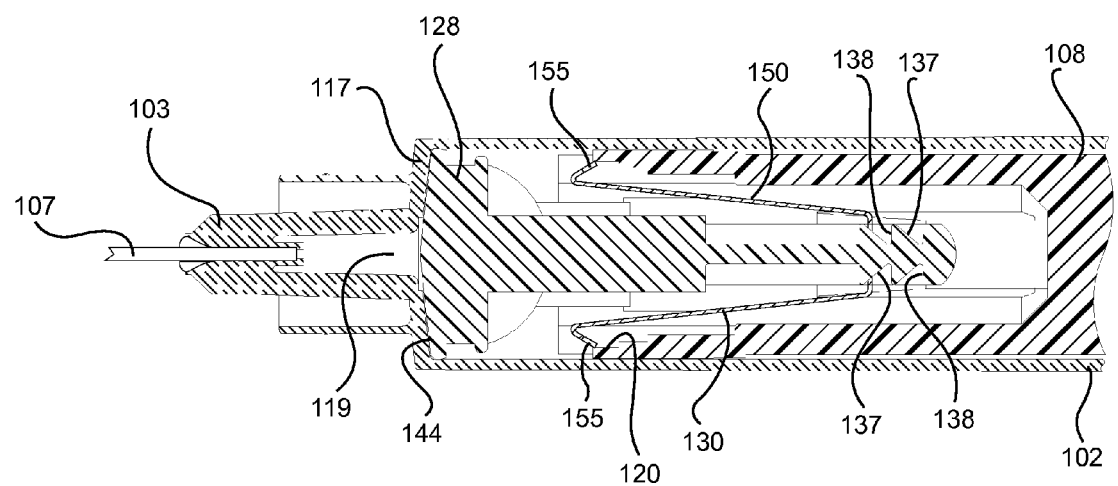
FIG. 14 is an enlarged partial cross-sectional view of the syringe assembly of FIG. 1 taken along line 3-3 showing the syringe assembly at the start of a second aspiration stroke.
Figure 14A:
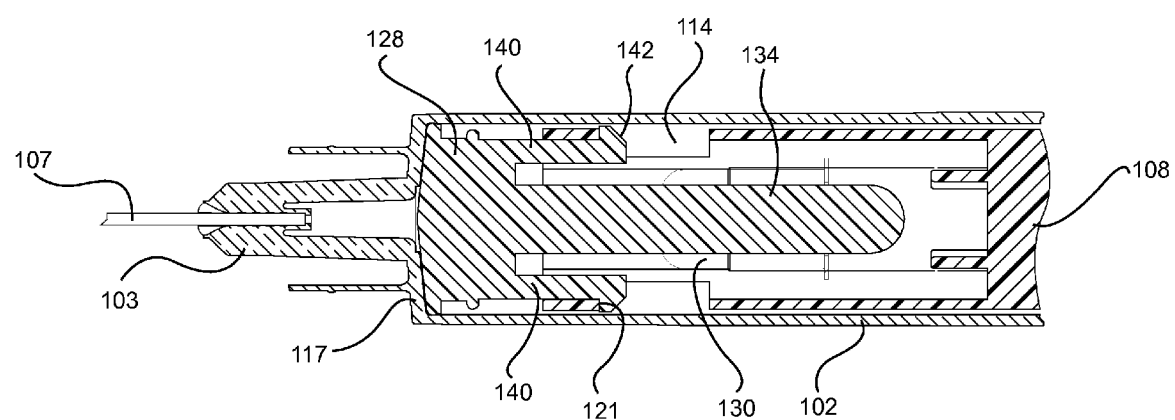
FIG. 14A is an enlarged partial cross-sectional view similar to FIG. 14 but rotated 90°.

When the diluent and the lyophilized medication are mixed the syringe assembly of the present invention may now be used to withdraw the reconstituted, ready-to-inject medication into the chamber of the syringe barrel, as best illustrated in FIGS. 14 and 14A, by applying a proximally directed force to the plunger rod while holding the syringe barrel. Proximally directed force will cause the plunger rod to move in a proximal direction while locking element 130 will remain relatively stationary due to its connection to the boss detent on the stopper. Proximal motion of the plunger causes the locking element to move distally along the inside surface of the plunger rod so that the sharp free end 155 of the cantilever legs moves from the proximal-most axially-spaced steps 120 in the plunger rod to the second more distal axially-spaced steps 120. Proximal motion of the plunger rod also causes outwardly extending ribs 142 of cantilever arms 140 to engage distal surfaces 121 of recesses 114 in the plunger rod so that the stopper now moves proximally with the plunger rod drawing the reconstituted medication into the chamber of the syringe barrel to an amount determined by the user. An advantage of the present invention is that the amount of medication drawn into the chamber, and therefore the maximum amount of medication that can be delivered, is determined by the user at the time of use and not by the placement of the components at the time of manufacture.

Figure 15:
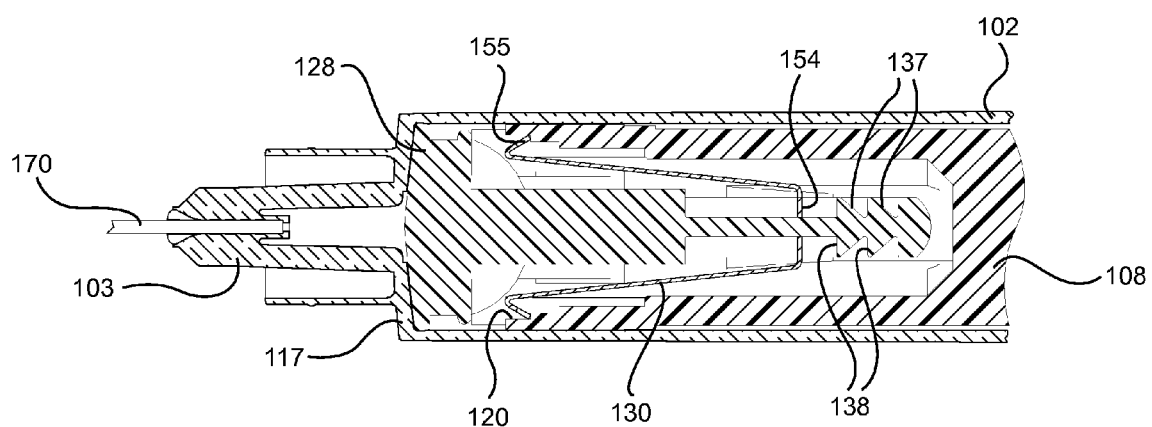
FIG. 15 is an enlarged partial cross-sectional view of the syringe assembly of FIG. 1 taken along line 3-3 showing the syringe assembly after a second dispensing stroke.
Figure 15A:
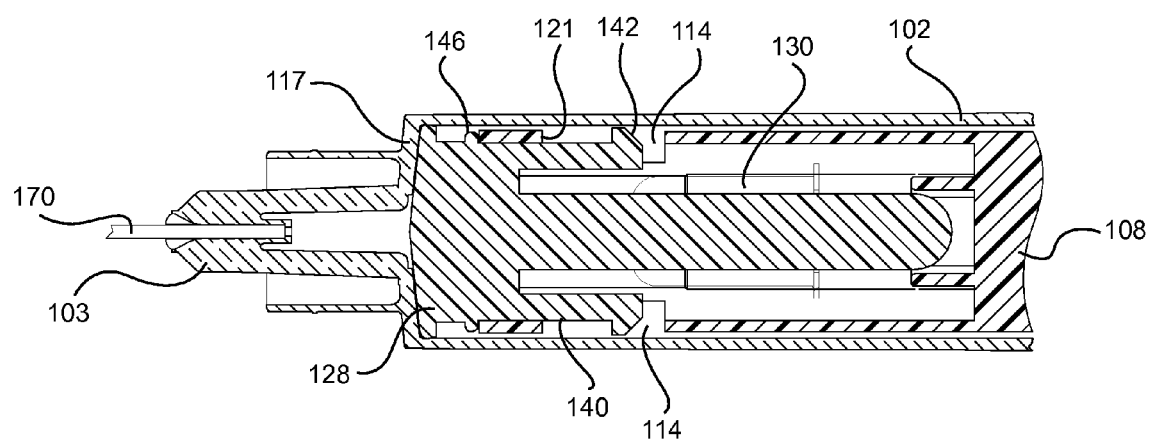
FIG. 15A is an enlarged partial cross-sectional view similar to FIG. 15 but rotated 90°.

The syringe assembly of the present invention is now ready for a second and final dispensing stroke which is best illustrated in FIGS. 15-15A. The medication is delivered to the patient by applying a distally directed force to the plunger rod causing the plunger rod to move in a distal direction with respect to the barrel. As the plunger rod advances in a distal direction the engagement of sharp free ends 155 of the locking element with the distal-most blunt surfaces 122 of axially-spaced steps 120 moves the locking element distally so that finger elements 154 of the locking element ride over the distal-most inclined surface 137 of the boss detents distally past the most distal boss detent 136. When the distally moving plunger rod contacts the stopper, both the stopper and the plunger rod move toward the distal end of the barrel to discharge the contents of the chamber through the passageway.

Figure 16:
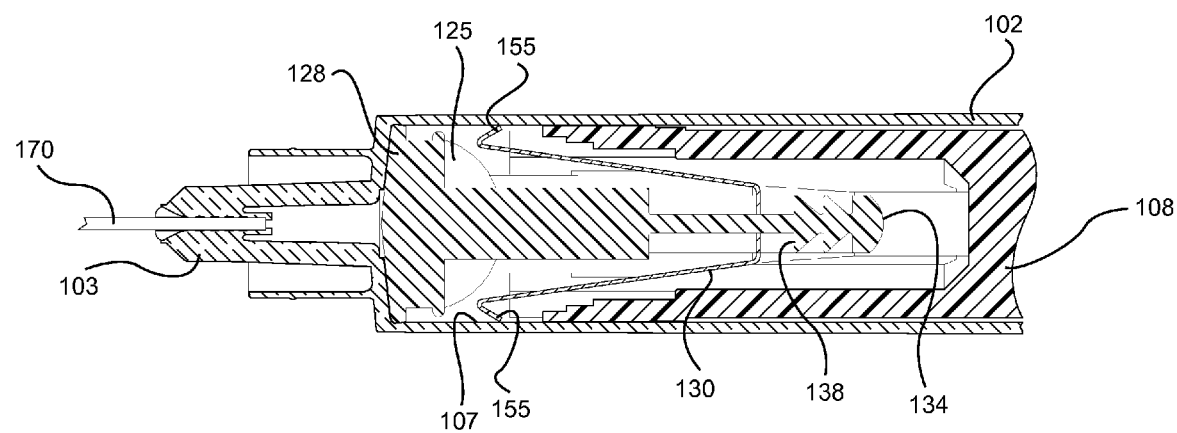
FIG. 16 is an enlarged partial cross-sectional view of the syringe assembly of FIG. 1 taken along line 3-3 showing a position of the internal components in the event of an attempt to withdraw the plunger rod after the second dispensing stroke.
Figure 16A:
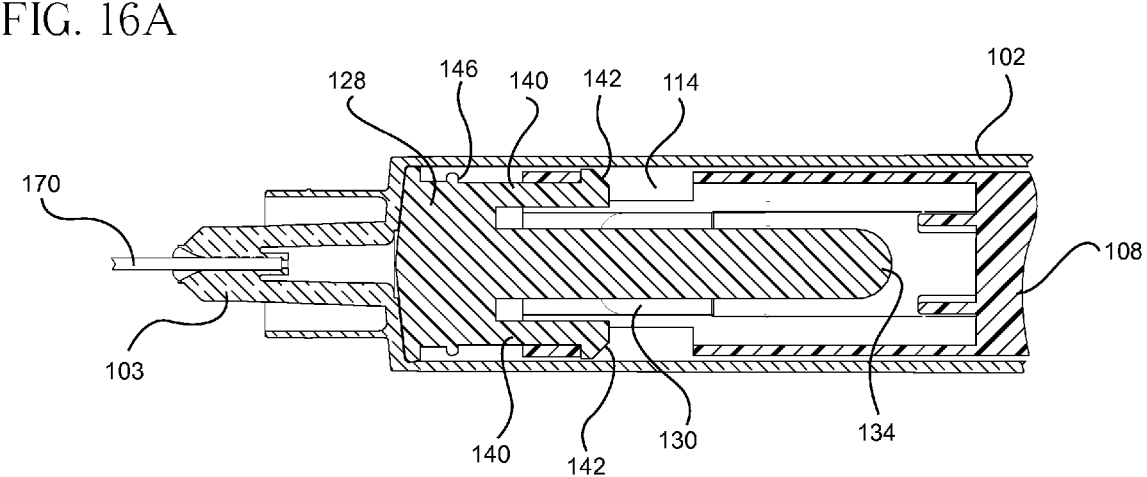
FIG. 16A is an enlarged partial cross-sectional view similar to FIG. 16 but rotated 90°.
Figure 17:
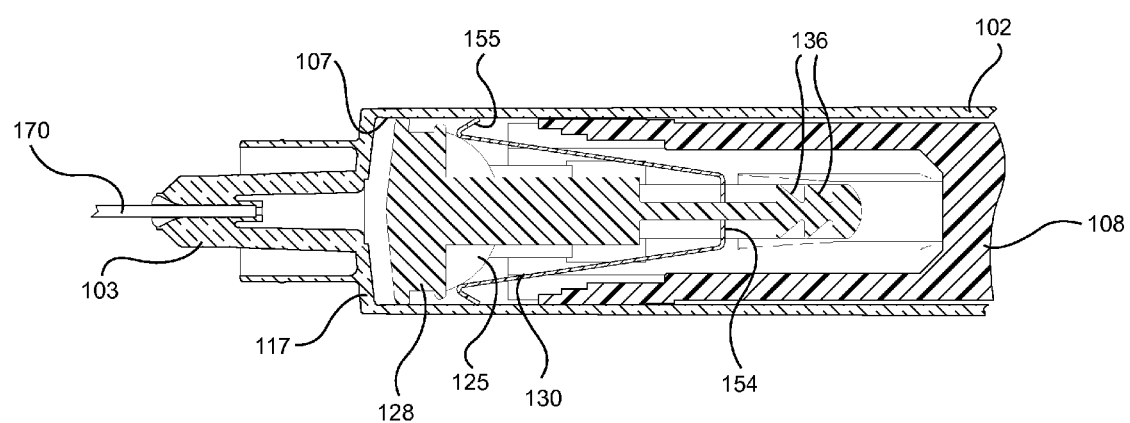
FIG. 17 is an enlarged partial cross-sectional view similar to the syringe assembly of FIG. 16 showing the interaction of additional structure to prevent reuse.
Figure 17A:
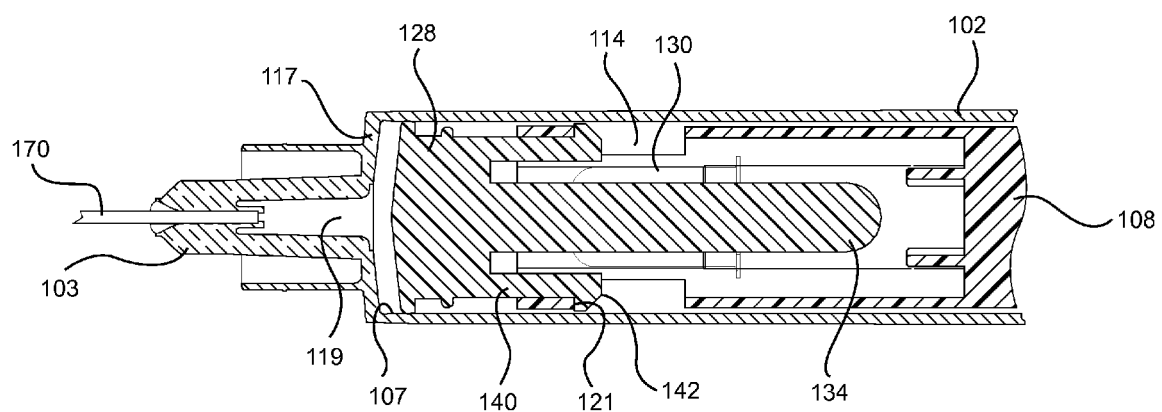
FIG. 17A is an enlarged partial cross-sectional view similar to FIG. 17 but rotated 90°.

The syringe assembly has now been used and is ready to be discarded. Any attempt to move the plunger rod in a proximal direction to refill the syringe assembly for further use will cause the locking element to disable the syringe. Specifically, as best illustrated in FIGS. 16 and 16A, moving the plunger rod in a proximal direction will allow the plunger rod to move a short distance until the sharp free ends 155 of the locking clip snap past the end of the plunger rod and engage the inside surface 107 of the barrel side wall. Further proximal motion of the plunger will be resisted by the locking element's engagement to the inside surface of the barrel sidewall. In addition, as illustrated in FIG. 17, cam surface 125 on the stopper is positioned to force sharp free ends 155 further into the syringe barrel wall as more proximally directed force is used in an attempt to improperly reuse the syringe. Accordingly, increased force to pull the plunger rod out of the syringe barrel results in increased force of engagement of the sharp free ends of the locking element into the barrel. It is desirable to provide a cut-out area 126 in the distal end of the plunger rod along the path of the sharp free ends of the locking element for supporting the locking element and allowing it to engage the inside surface of the barrel. Further, the area at the end of the plunger rod on the area around the cutout can be configured to support the locking element so that if the user accidentally withdraws the plunger rod a second time before delivering the final dose of medication the medication may still be delivered even though the locking element sharp free ends are touching the barrel so long as they are moved in a distal direction and urged not to engage the inside surface of the barrel by the cut-out area and the plunger rod. In this case the area around the cutout supports and limits the motion and helps prevent deformation of the sharp free end of the locking element.

Figure 18:
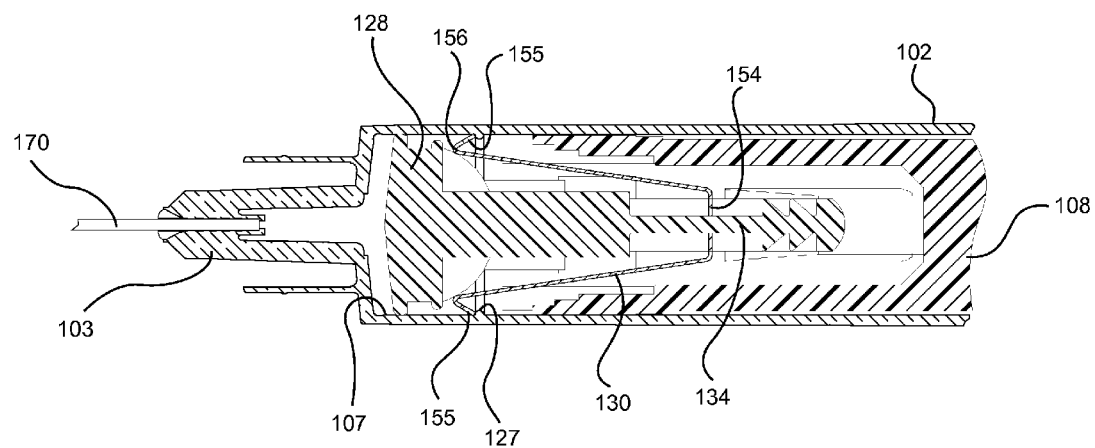
FIG. 18 is an enlarged partial cross-sectional view similar to the syringe assembly of FIG. 17 showing a discontinuity in the syringe barrel for engaging the locking element.
Figure 19:
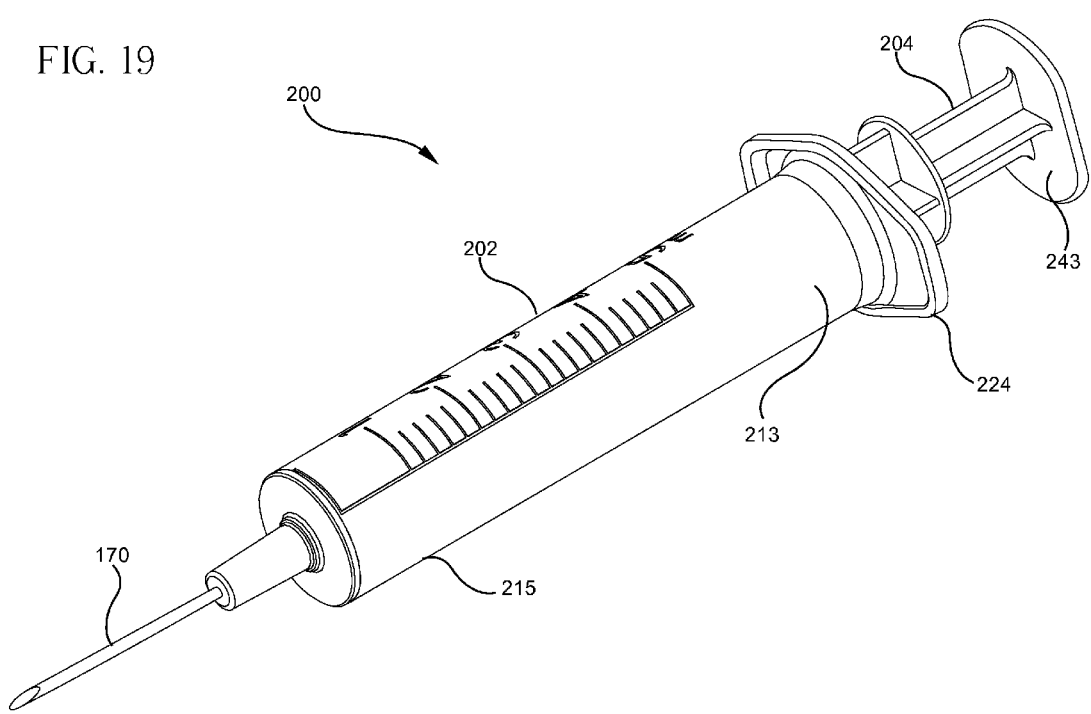
FIG. 19 is a perspective view of an alternative syringe assembly of the present invention having a needle attached to the barrel.
Figure 20:
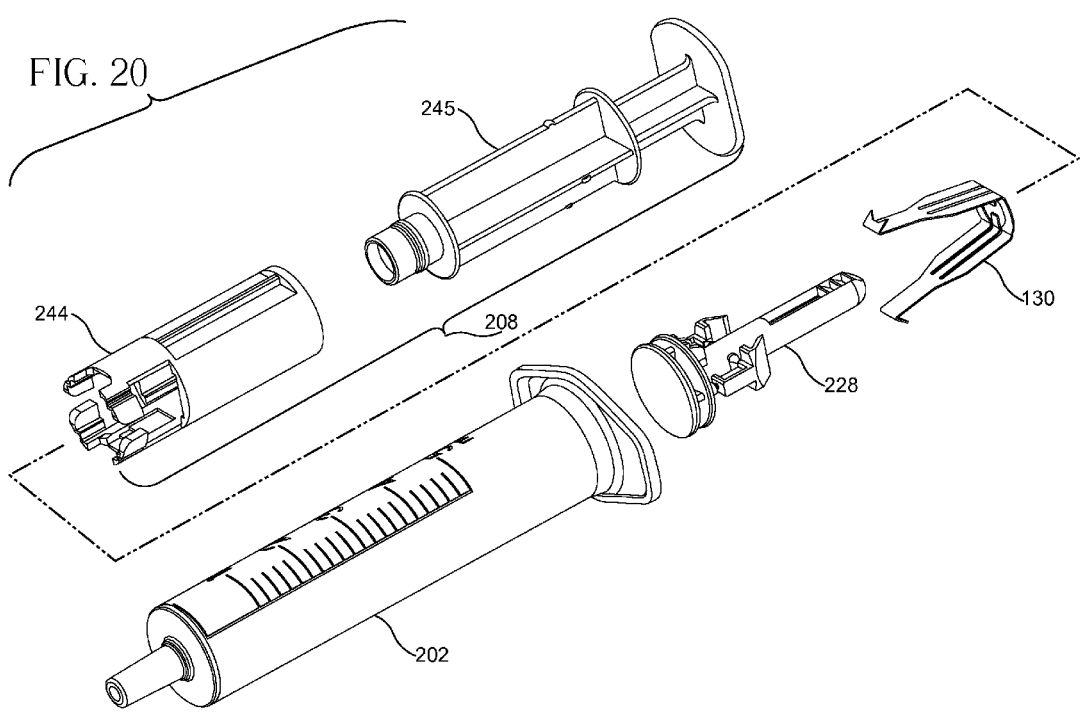
FIG. 20 is an exploded view of the alternative syringe assembly of FIG. 19.
Figure 21:
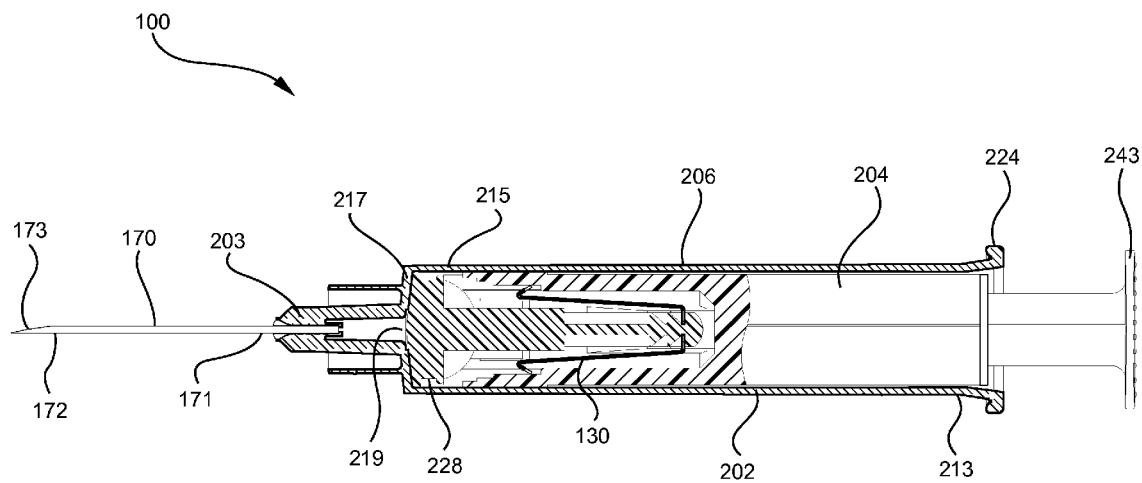
FIG. 21 is an enlarged cross-sectional view of the syringe of FIG. 1 including the needle cannula.
Figure 22:
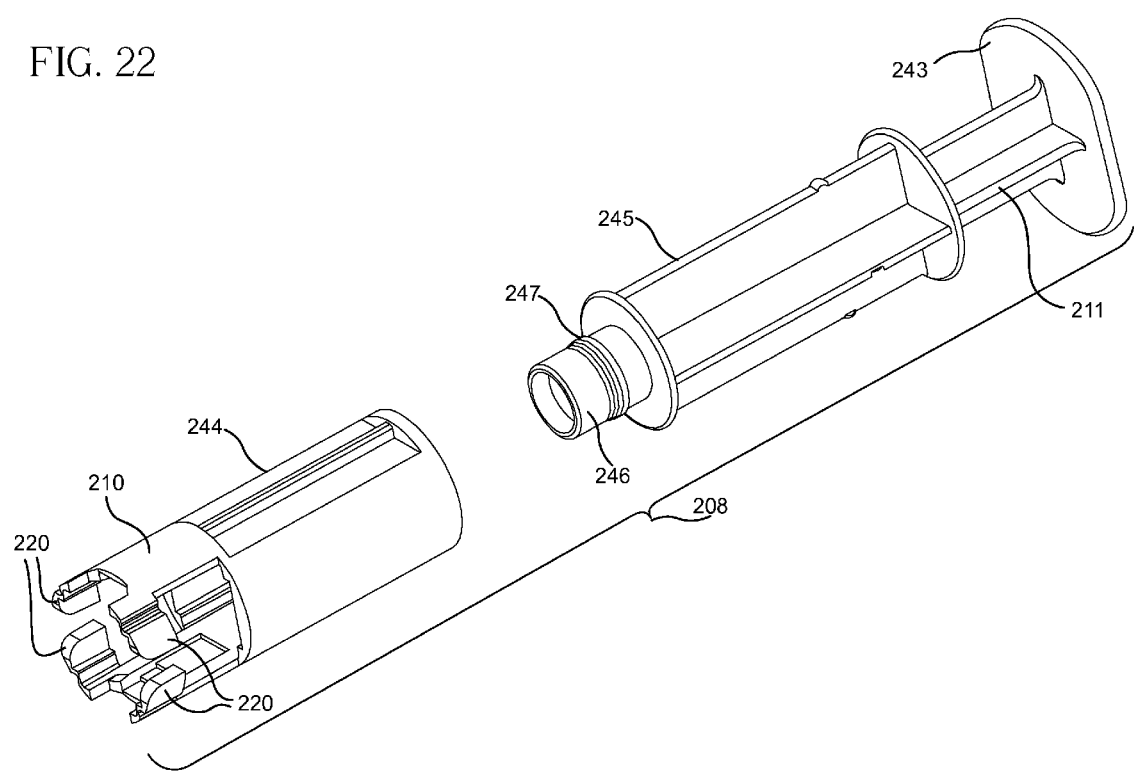
FIG. 22 is a perspective view of the assembled plunger rod including the proximal portion and the distal portion of the plunger rod.
Figure 23:
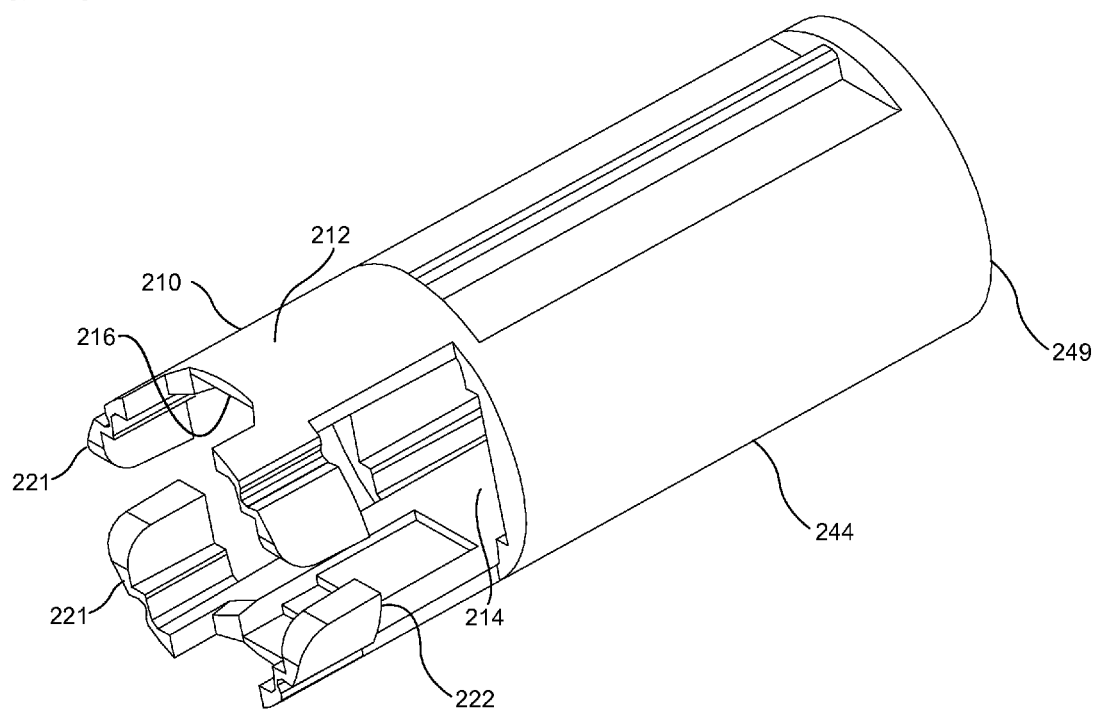
FIG. 23 is a perspective view of the distal portion of the plunger rod.
Figure 24:
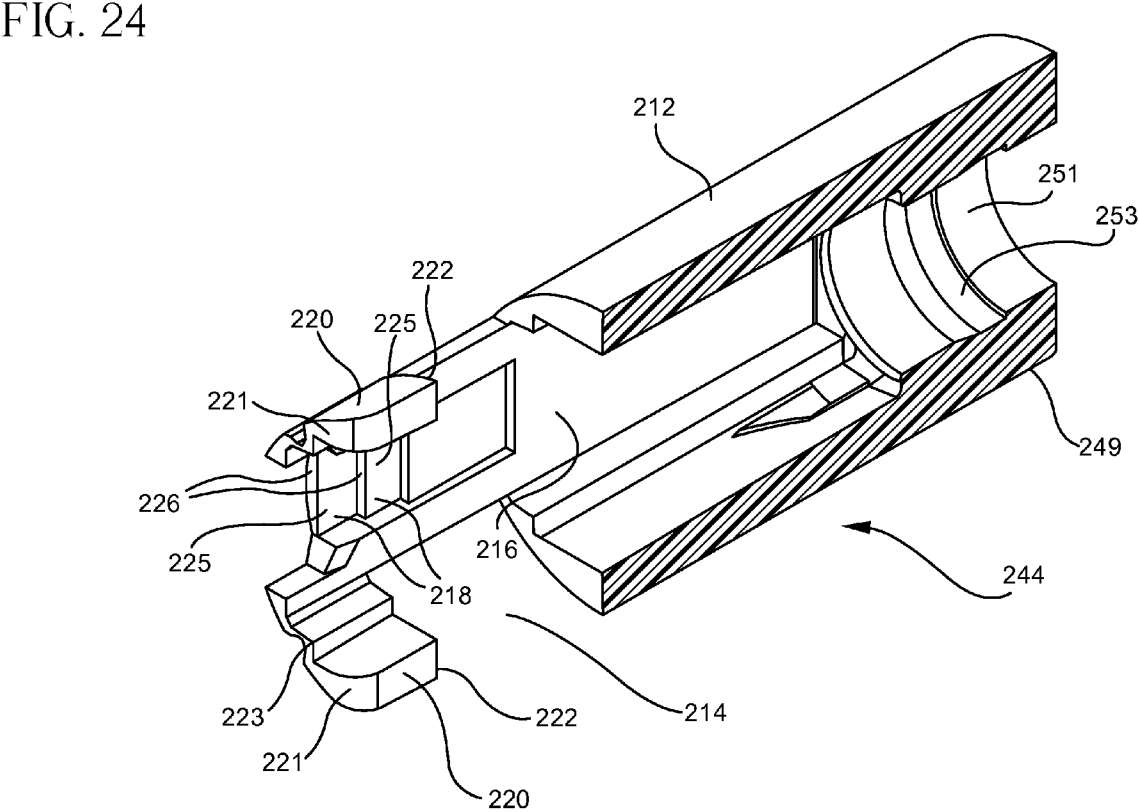
FIG. 24 is a cross-sectional view of the distal portion of the plunger rod of FIG. 23 taken along line 24-24.
Figure 25:
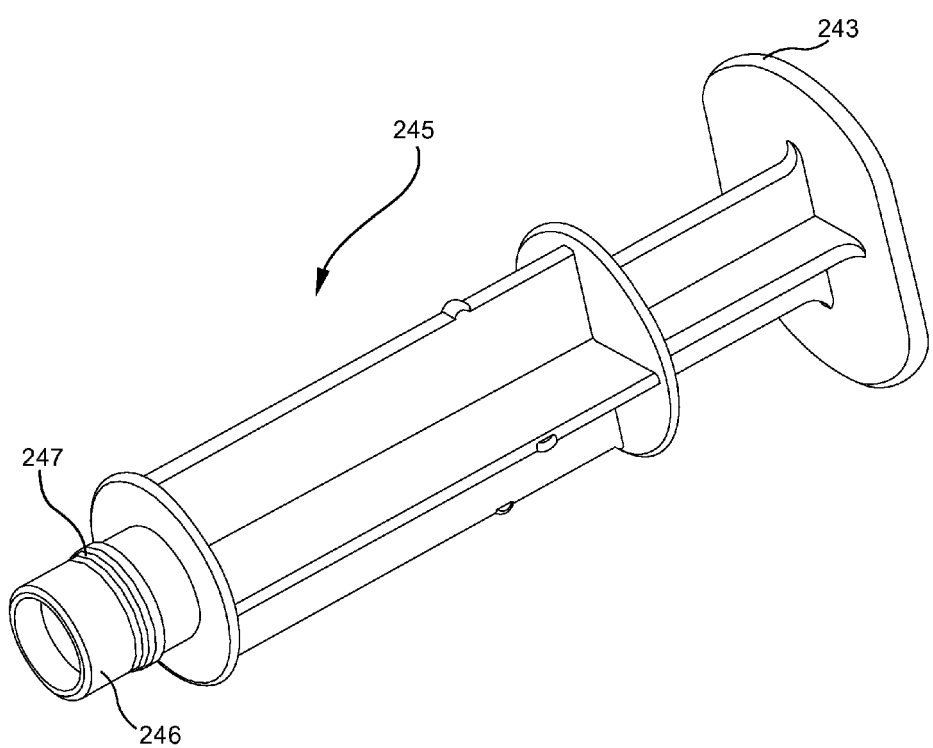
FIG. 25 is a perspective view of the proximal portion of the plunger rod.
Figure 26:
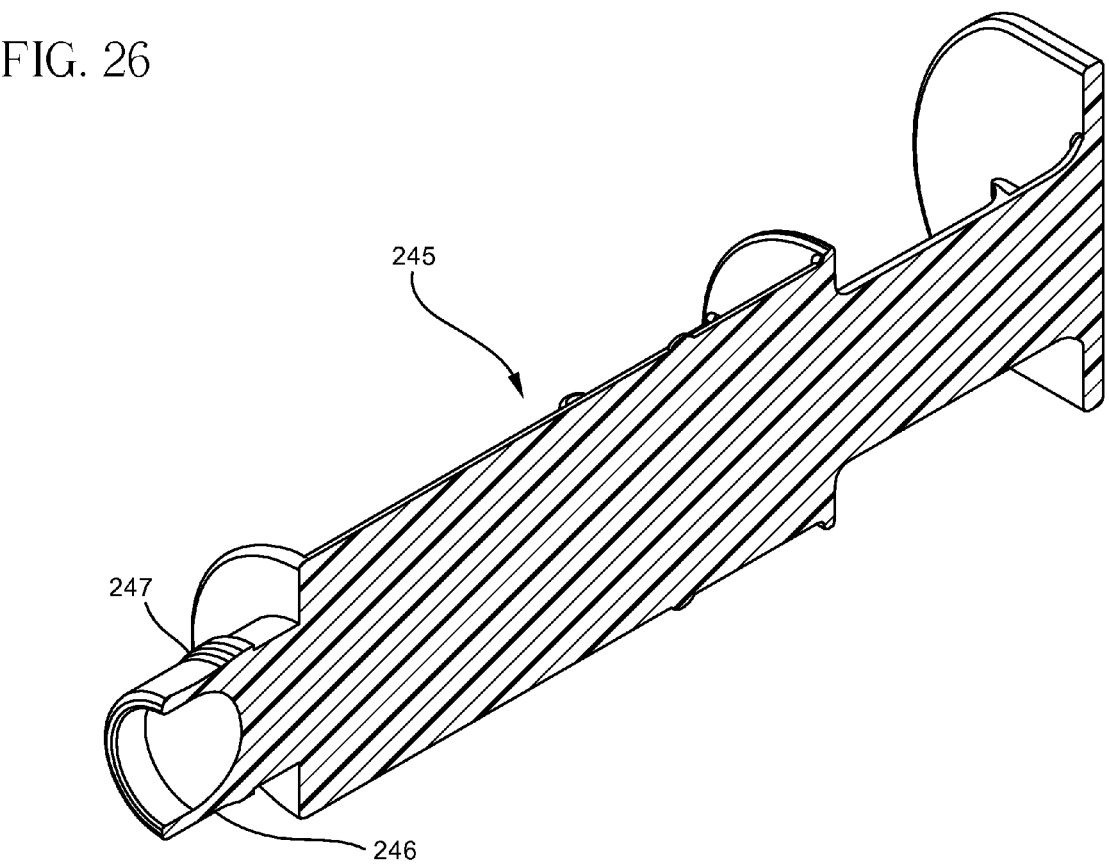
FIG. 26 is a cross-sectional view of the proximal portion of the plunger rod of FIG. 25 taken along line 25-25.
Figure 27:
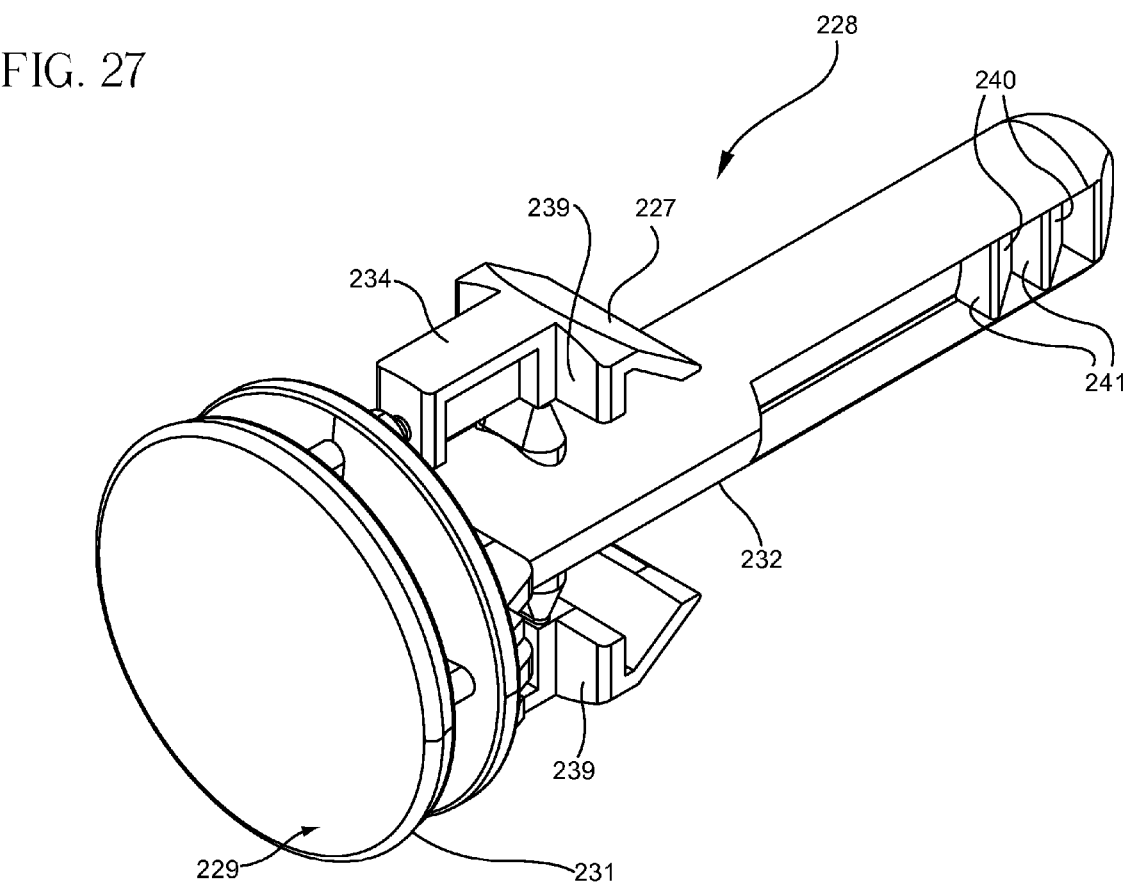
FIG. 27 is a perspective view of the stopper as viewed from the distal end.
Figure 28:
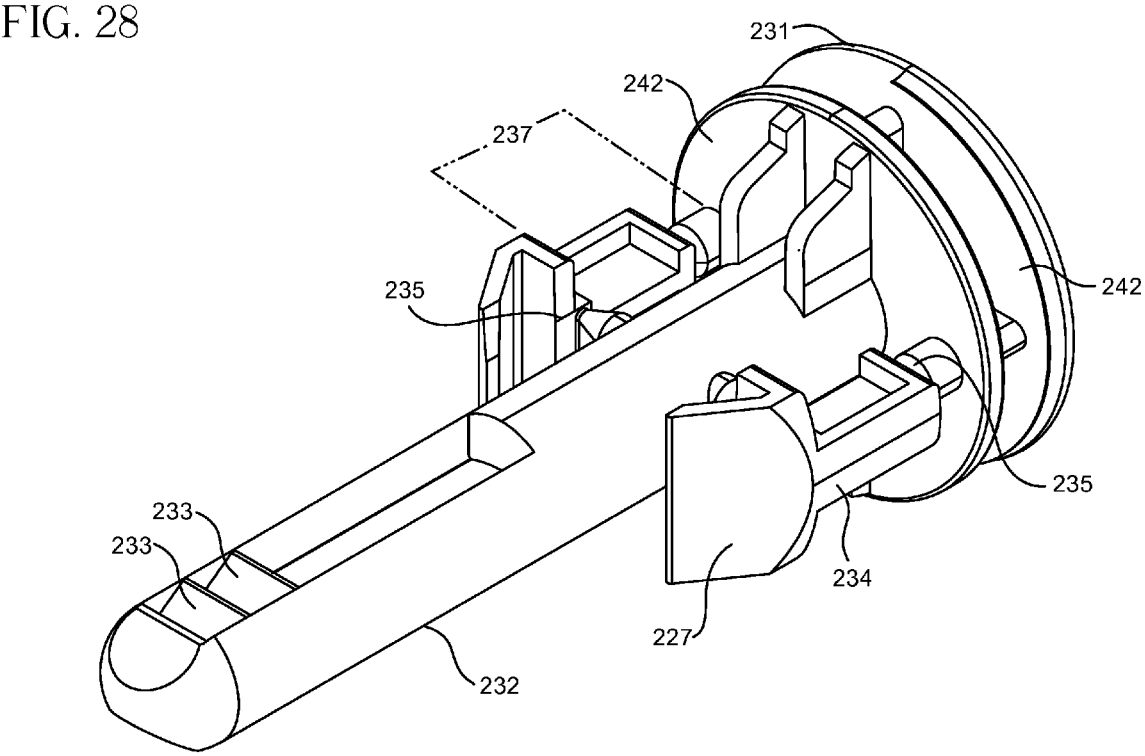
FIG. 28 is a perspective view of the stopper as viewed from the proximal end.
Figure 29:
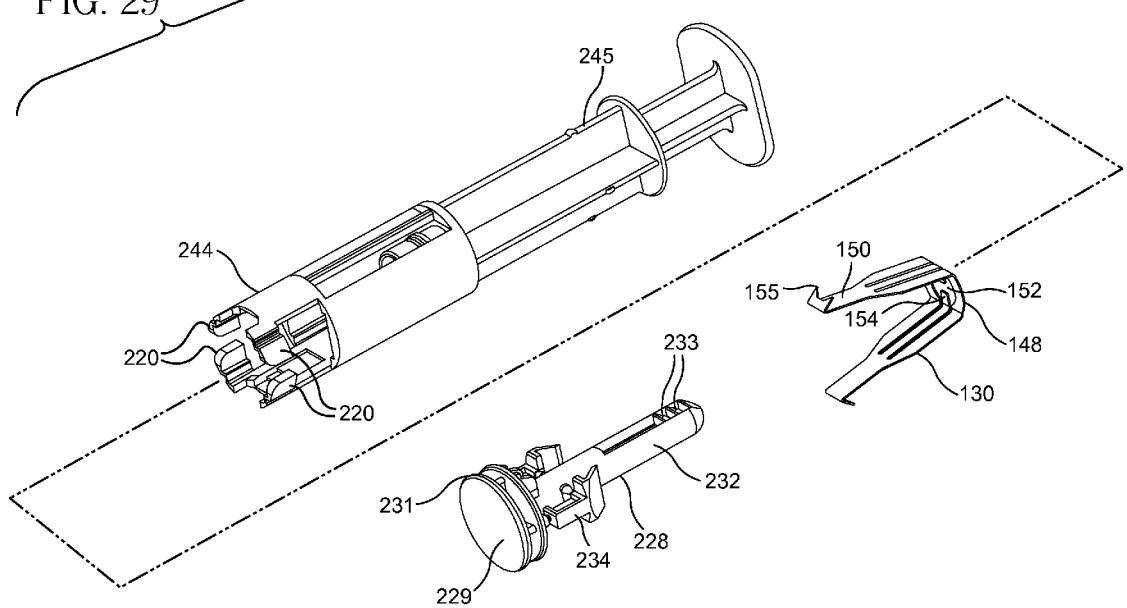
FIG. 29 is an enlarged exploded view of the stopper, locking element and plunger rod.
Figure 30:
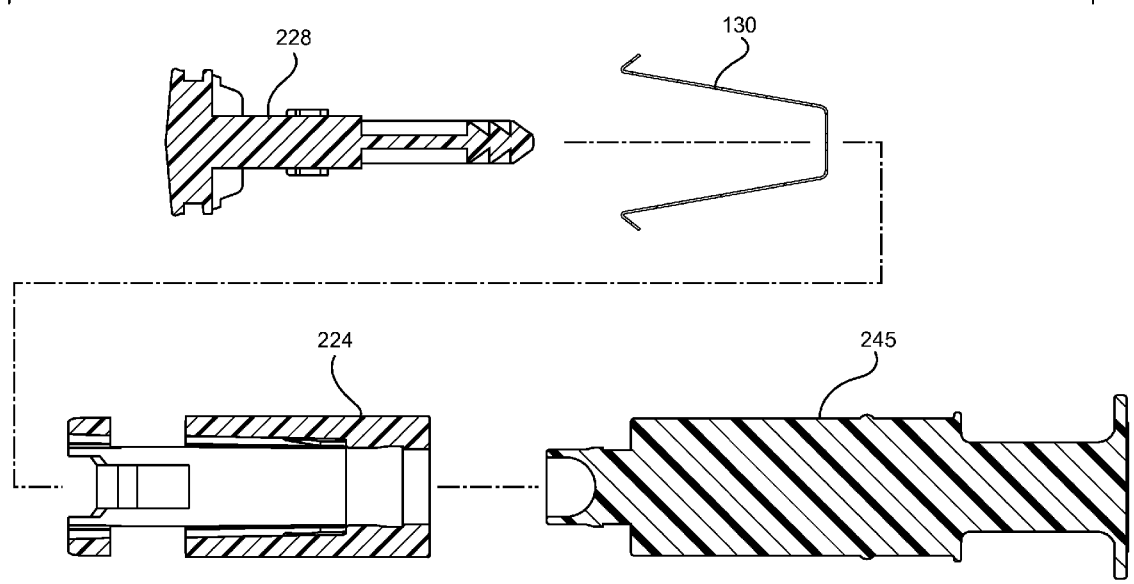
FIG. 30 is a side-elevational, cross-sectional view of the stopper, locking clip and plunger rod of FIG. 29.

It is also within the purview of the present invention to provide a discontinuity such as a recess or projection on the interior surface of the barrel, as illustrated in FIG. 18, to further improve the engagement of the sharp free end of the locking element with the interior surface of the barrel. In FIG. 18 syringe barrel 102 includes a discontinuity in the form of an inwardly directed projection 127 on inside surface 107 of the barrel. In this embodiment, projection 127 is an annular ring projecting into the barrel and extending 360° around the inside surface. The discontinuity may be in the form of an annular projection, an annular recess or one or more projections or recesses shaped to engage locking element, all positioned within the barrel to engage sharp free end 155 of locking element 130 to further increase the grip of the locking element on the barrel and inside surface.

The present syringe assembly provides an improvement over prior art devices by allowing a variable dose of diluent, chosen by the user at the time of use, to be drawn into the syringe, dispensing the diluent into a vial containing a substance to be reconstituted, drawing a selected amount of the reconstituted substance back into the syringe and then delivering the contents of the syringe. The selected amount of the reconstituted substance may be equal or less than the full volume reconstituted at the discretion of the user. The syringe assembly is automatically disabled after the final injection stroke by reversing the direction of the movement of the plunger rod from the dispensing direction to the aspirating direction. After the injection stroke of the syringe plunger the plunger rod is retracted to activate the disabling mechanism to prevent axial movement of the stopper toward the proximal end of the syringe barrel thereby preventing the stopper from being removed and preventing reuse of the syringe.

When the present syringe assembly has two or more detents on the stopper and in the plunger rod, the maximum number of strokes the syringe assembly will allow can be varied by the initial position of the locking element with respect to the stopper detents and the plunger rod detents.

Referring to the drawings, in particular FIGS. 19-38, which illustrate an alternative embodiment of the syringe assembly of FIGS. 1-18. From a user's viewpoint, the alternative embodiment of syringe assembly 200 functions similarly to the syringe assembly of FIGS. 1-18. However, syringe assembly 200 contains numerous structural and functional changes intended, primarily, to improve the tamper resistance of the syringe assembly.

Operable syringe assembly 200 includes a syringe barrel 202 and a plunger assembly 204. Barrel 202 includes a cylindrical sidewall 206 having an inside surface 207 defining a chamber 209 for retaining fluid, an open proximal end 213 and a distal end 215 including a distal wall 217 having a passageway 219 therethrough in fluid communication with the chamber. In this embodiment, the distal wall of the barrel includes an elongate tip 203 extending distally therefrom and having a passageway in fluid communication with the passageway in the distal wall. In this embodiment barrel 202 also includes a needle cannula 170 having a proximal end 171, a distal end 172 and a lumen 173 therethrough. The proximal end of the needle cannula is attached to elongate tip 203 so that the lumen of the needle cannula is in fluid communication with passageway 219 in the barrel.

Plunger assembly 204 includes an elongate hollow plunger rod 208, a stopper 228, and a locking element 130. Elongate plunger rod 208 includes a proximal end 211, an open distal end 210 having a side wall 212 with an interior surface 216. The interior surface includes at least one detent 218. The side wall includes an axial opening 214 and a positioning lug 220 projecting into the axial opening. The positioning lug includes a distal face 221 and a proximal face 222. In this embodiment, the at least one detent on the interior surface of the plunger rod includes four axially spaced detents 218 with two detents on each side of the plunger rod. Each pair of detents is preferably shaped to form axially spaced steps 225 with each step having a blunt surface 226 at its distal end extending inwardly from the interior surface of the plunger rod.

Stopper 228 includes a sealing element 229 having a peripheral surface 231 forming a seal with the inside surface of the barrel. A boss member 232 projects proximally from the sealing element. There is at least one boss detent on the boss, and in this embodiment there are two boss detents 233. The boss detents are axially spaced and preferably include an incline surface 240 extending proximally inwardly and a blunt surface 241 at the distal end of each of the inclined surfaces. The stopper includes at least one retaining element 234 connected to the stopper by a frangible connection 235 and defining an axial recess 237 having a proximal ledge 239 for accepting positioning lug 220 of the plunger rod and for limiting axial motion of the positioning lug in axial recess 237. In this embodiment, there are two retaining elements positioned on opposite sides of the boss member with each retaining element held in position preferably by three frangible connections. The frangible connections are preferably made of breakable protuberances joining the retaining elements to parts of the boss and/or sealing element. It is preferred that the frangible connections be integrally molded from plastic material. A wide variety of materials are suitable for molding the structure with polystyrene and polyethylene being preferred. The frangible connections can be anywhere along the interface of the various elements depending on the geometry of the components and the size and shape of the frangible connections. A frangible connection can also be made by connecting the elements with the frangible adhesive or by joining the parts as in a mechanical snap-fit arrangement. All of these possibilities are within the purview of the present invention with the integrally molded structure being preferred. The stopper is preferably integrally formed of thermoplastic material. The sealing element and/or the peripheral sealing surface thereon may be made of elastomeric materials.

Locking element 130 includes a central body portion 148 having an aperture 152 therethrough and at least one cantilevered leg 150 extending distally outwardly from the body portion and at least one finger element 154 extending inwardly from the aperture. In this embodiment, at least two cantilevered legs with each of the cantilevered legs having a sharp free end 155 directed outwardly for engaging the inside surface of the barrel. The configuration of sharp free end 155 can be any configuration capable of engaging the inside surface of the barrel, such as a sharp edge or one or more pointed teeth and the like.

In this embodiment, retaining element 234 of the stopper preferably includes a proximally and inwardly directed ramp surface 227. Also, plunger rod 208 preferably includes a flexible element 223 connecting each positioning lug and the sidewall of the plunger rod for allowing the positioning lug to flex outwardly during the assembly of the plunger assembly. The ramp surface on the stopper will contact the lugs on the plunger rod during assembly, forcing the lugs outwardly until they pass over said retaining element's proximal edge after which positioning lugs 220 can move into axial recess 237 on the stopper. As will be explained in more detail hereinafter, the axial recess is longer than the axial length of the positioning lugs and this relationship provides relative axial motion, or lost motion, between the plunger rod and the stopper.

Figure 31:
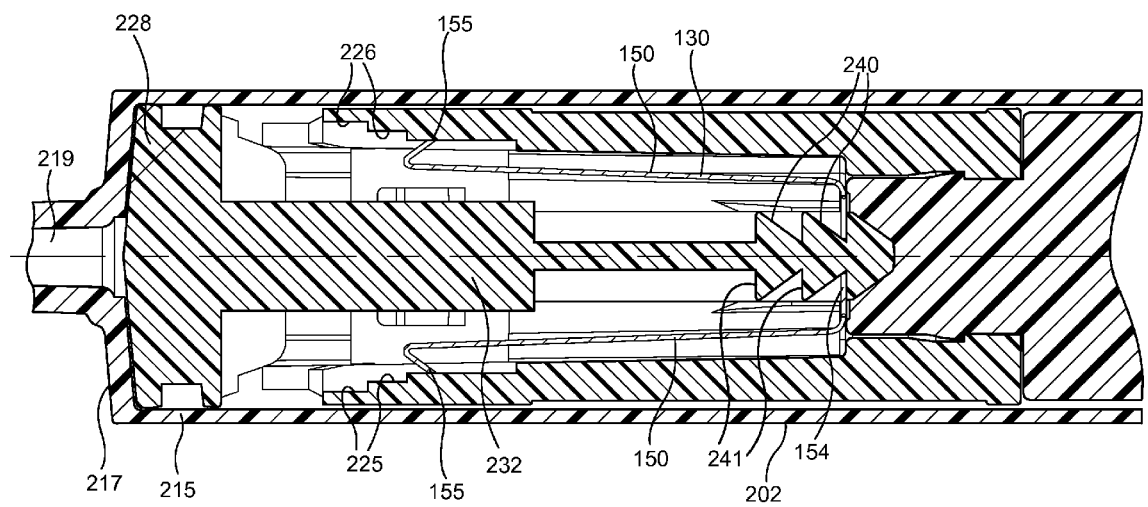
FIG. 31 is an enlarged partial cross-sectional view of the syringe assembly of FIG. 19, taken along line 21-21 showing the syringe assembly before use.
Figure 31A:
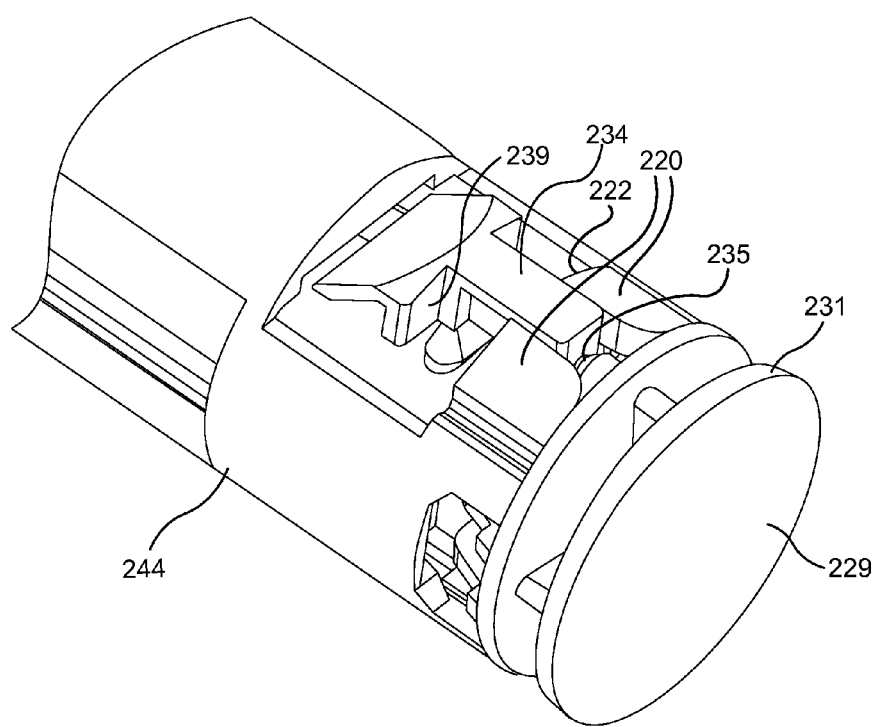
FIG. 31A is an enlarged partial perspective view similar to FIG. 31 but rotated 90°.

In the initial position of the syringe, as best illustrated in FIGS. 31 and 31A, locking element 130 is positioned with its sharp-free ends 155 contacting the interior surface of the plunger rod proximally of axially spaced steps 225. Boss member 232 is positioned in aperture 152 of locking element 130 so that finger elements 154 contact the boss member proximally of boss detents 233. Positioning lugs 220 are positioned in axial recesses 237 of the stopper. The positioning lugs are configured to complement the axial recesses in the stopper to allow limited axial movement of the stopper with respect to the plunger rod. The position illustrated in FIGS. 31 and 31A, syringe assembly 200 is ready for use for drawing liquid into the chamber of the barrel.

As will be shown, the operation of the plunger assembly of this embodiment includes a first aspiration stroke followed by a first dispensing stroke, a second aspiration stroke and a final dispensing stroke after which the syringe can be disabled. The disabling elements prevent or inhibit movement of the stopper in a proximal aspirating direction thereby limiting the function of the syringe assembly to a single use. The maximum number of strokes being limited by a number of axially positioned detents in the plunger rod and the number of axially positioned boss detents on the stopper. However, the actual number of strokes the syringe may make will be determined by the position of the locking element with respect to the detents in the plunger rod and the detents on the stopper at the time of first use. For example, a syringe with two plunger detents and two stopper detents can be supplied to the end user as a syringe capable of two strokes or four strokes.

Figure 32:
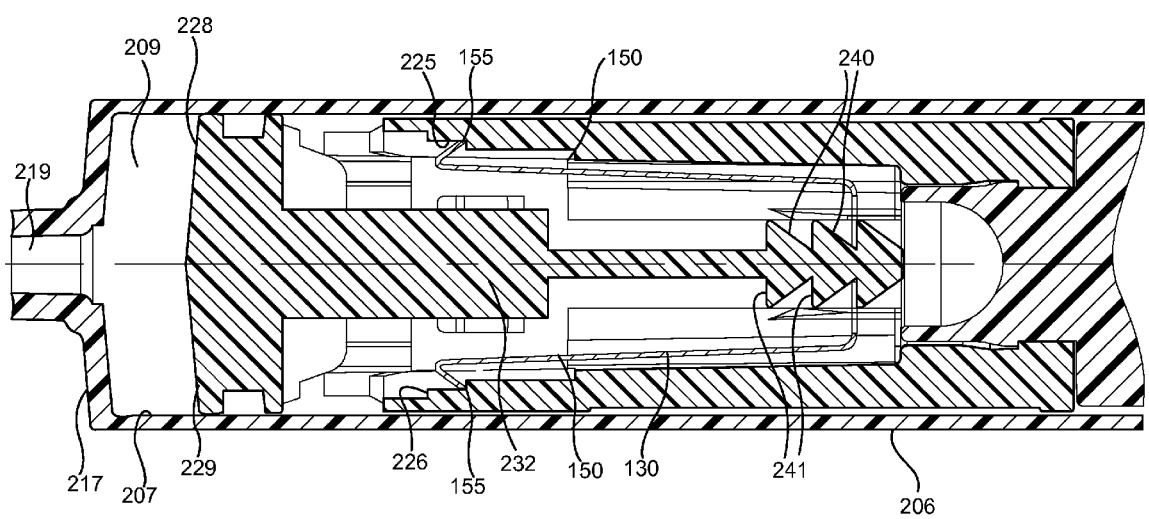
FIG. 32 is an enlarged partial cross-sectional view of the syringe assembly of FIG. 19 taken along line 21-21 showing the syringe assembly after a first aspiration stroke.
Figure 32A:
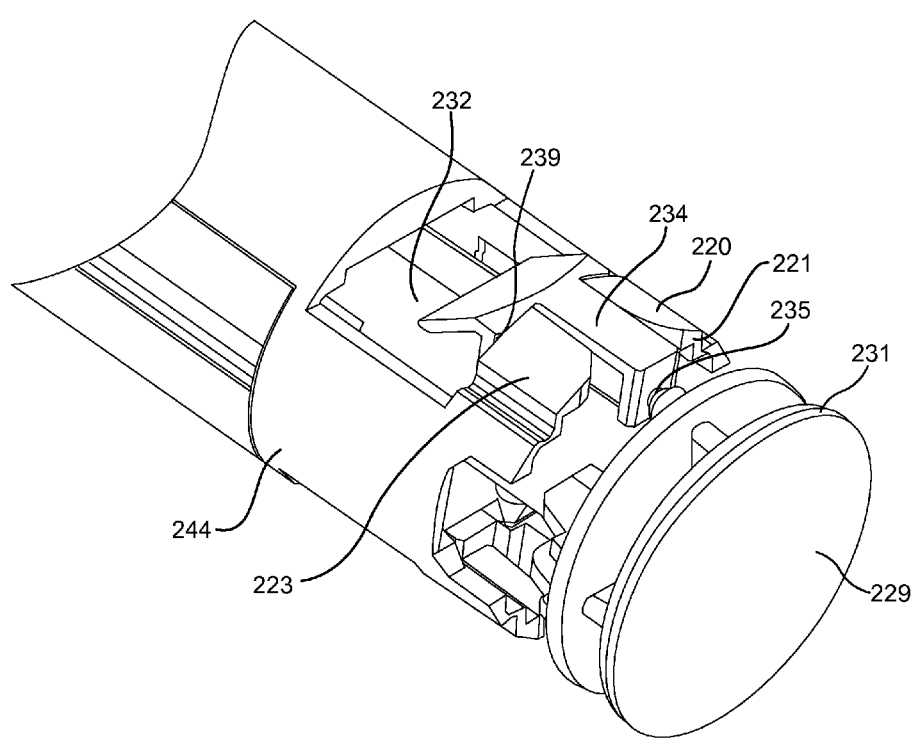
FIG. 32A is an enlarged partial perspective view similar to FIG. 32 but rotated 90°.

The syringe assembly may now be used to draw liquid, such as sterile water, diluent into the chamber of the barrel by applying a proximally directed force to a thumb-press 243 on the proximal end of the plunger rod while holding the syringe barrel. As illustrated in FIGS. 32 and 32A, this causes the plunger rod to move proximally with respect to the stopper until the free end of the cantilevered legs 150 move distally along inner surface of the plunger rod and snap past blunt surface 226 of the proximal-most axially spaced step 225, as best illustrated in FIG. 32. Also, during this first aspiration stroke, when proximal surface 222 of positioning lug 220 contacts proximal ledge 239 of retaining element 234 the stopper is drawn proximally with respect to the barrel as the plunger rod moves proximally as best illustrated in FIG. 32A. The stopper is now moved proximally, through the action of the plunger rod, until the desired volume of liquid is in the chamber, as determined by the user.

Figure 33:
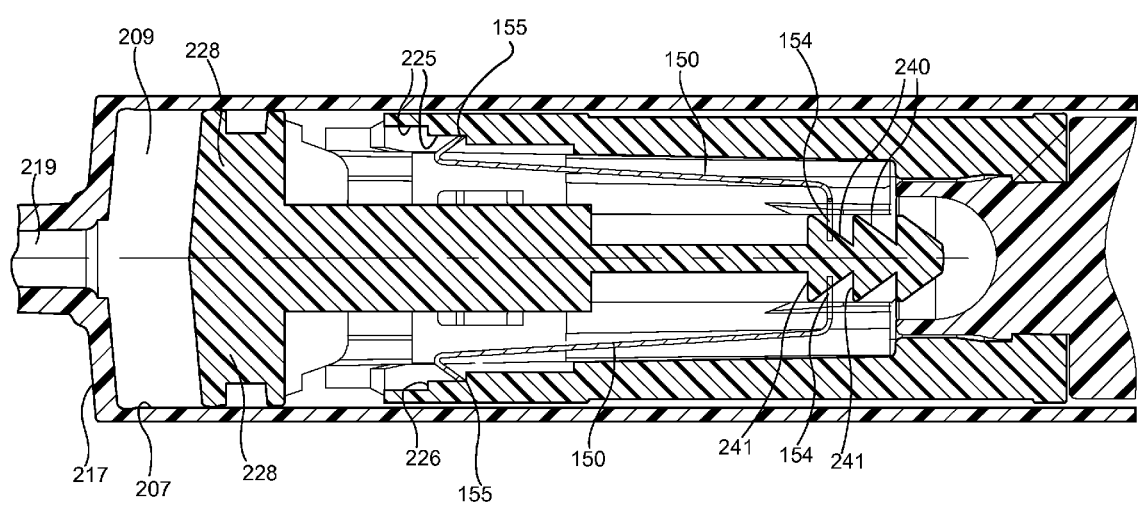
FIG. 33 is an enlarged partial cross-sectional view of the syringe assembly of FIG. 19 taken along line 21-21 showing the syringe assembly during a first dispensing stroke.

The liquid diluent in the chamber may now be discharged into a vial of dry medication such as lyophilized medication for reconstitution. This first dispensing stroke is accomplished by moving the plunger rod in a distal direction while holding the barrel. A barrel flange 224 is provided on the proximal end of the barrel to help control motion of the barrel during use of the syringe assembly. As best illustrated in FIGS. 33 and 31A, as the plunger rod moves distally, locking element 130 moves with the plunger rod dragging the locking element with it so that finger elements 154 on the locking element slide from the proximal-most to the distal-most boss detent by riding up incline surface 240 and falling into the second detent. When the plunger rod contacts the stopper, the stopper will begin moving in a distal direction along with the plunger rod to discharge liquid diluent from the chamber into, for example, a vial of lyophilized medication.

Figure 34:
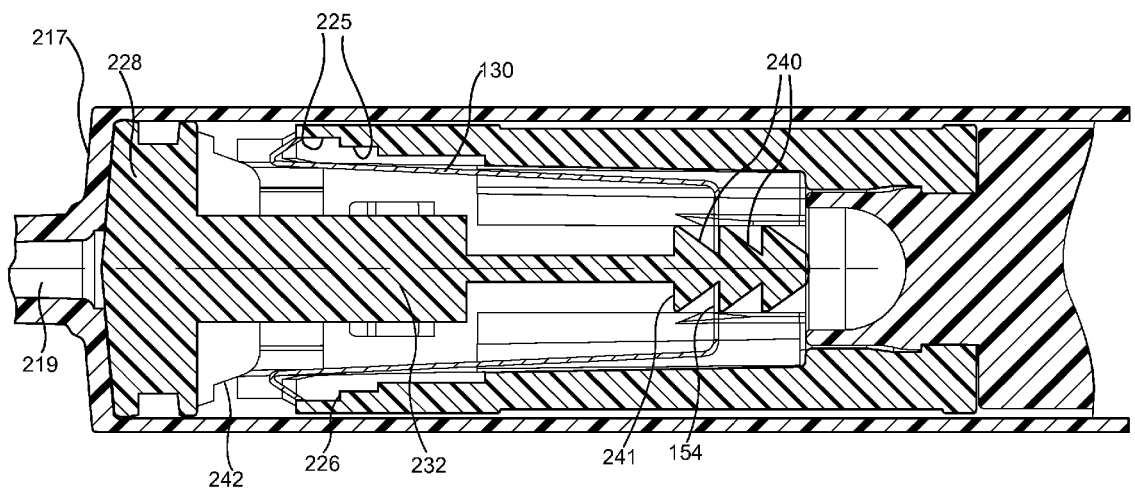
FIG. 34 is an enlarged partial cross-sectional view of the syringe assembly of FIG. 19 taken along line 21-21 showing the syringe assembly at the start of a second aspiration stroke.

When the diluent and the lyophilized medication are mixed, the syringe assembly of the present embodiment may now be used to withdraw the reconstituted, ready-to-inject medication into the chamber of the syringe barrel, as best illustrated in FIGS. 34 and 32A, by applying a proximally directed force to the plunger rod while holding the syringe barrel. This proximally directed force will cause the plunger rod to move in a proximal direction while locking element 130 will remain relatively stationary due to its connection to the boss detent on the stopper. Proximal motion of the plunger rod causes the locking element to move distally along the inside surface of the plunger so that the sharp-free end 155 of the cantilevered legs moves from the proximal-most axially-spaced step 225 to the distal-most step 225. Proximal motion of the plunger rod also causes proximal face 222 of the positioning lug on the plunger rod to contact proximal ledge 239 of the stopper retaining element 234 so that the stopper now moves proximally with the plunger rod drawing the reconstituted medication into the chamber of the syringe barrel to an amount determined by the user. An advantage of the present invention is that the amount of medication drawn into the chamber, and therefore the maximum amount of medication that can be delivered, is determined by the user at the time of use and not by the placement of the components at the time of manufacture.

Figure 35:
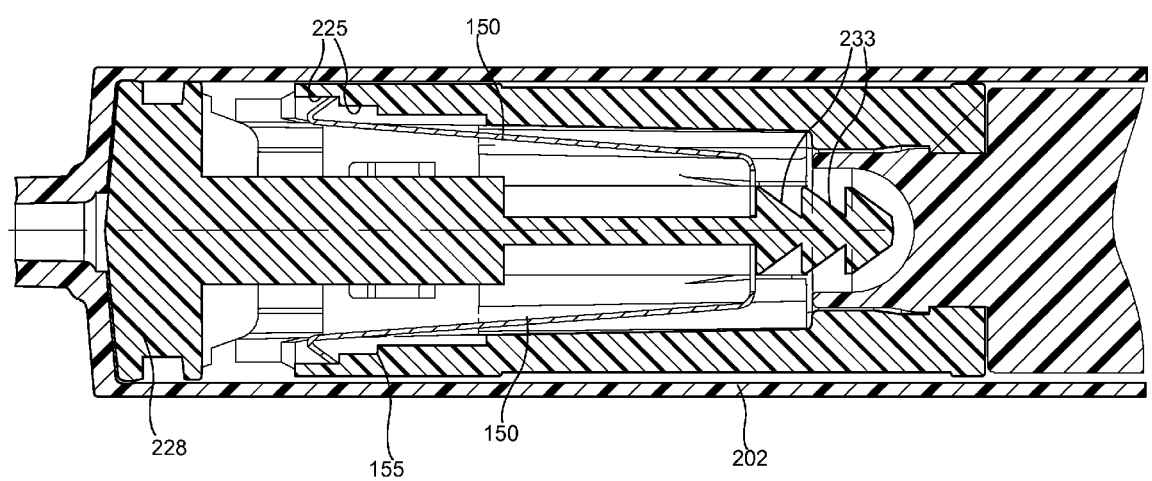
FIG. 35 is enlarged partial cross-sectional view of the syringe assembly of FIG. 19 taken along line 21-21 showing the syringe assembly after a second dispensing stroke.

The syringe assembly of the present invention is now ready for a second and final dispensing stroke as best illustrated in FIGS. 35 and 31A. The medication is delivered to the patient by applying a distally directed force to the plunger rod causing the plunger rod to move in a distal direction with respect to the barrel. As the plunger rod advances in a distal direction the engagement of sharp-free ends 155 of the locking element with the distal-most blunt surface 226 of the axially-spaced steps 225 move the locking element distally so that finger elements 154 of the locking element ride over the distal-most inclined surface 240 of the boss detents distally past the most distal boss detent 233. When the distally moving plunger rod contacts the stopper, as illustrated in FIG. 31A, both the stopper and the plunger rod move toward the distal end of the barrel to discharge the contents of the chamber through the passageway.

Figure 36:
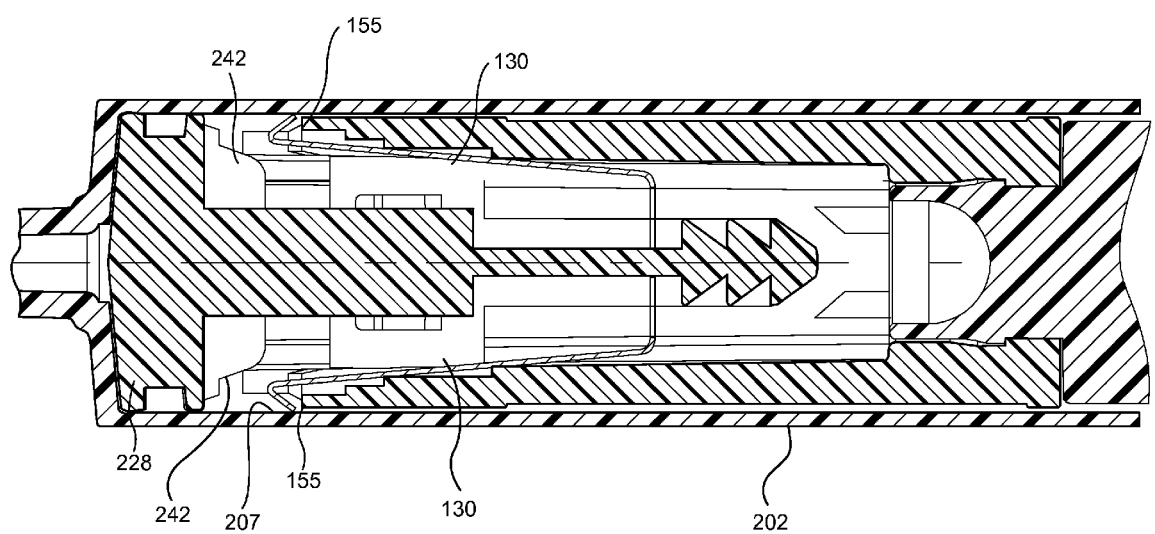
FIG. 36 is an enlarged partial cross-sectional view of the syringe assembly of FIG. 19 taken along line 21-21 showing a position of the internal components in the event of an attempt to withdraw the plunger rod after the second dispensing stroke.

The syringe assembly has now been used and is ready to be discarded. Any attempt to move the plunger rod in the proximal direction to refill the syringe assembly for further use will cause the locking element to disable the syringe. Specifically, as best illustrated in FIGS. 36 and 32A, moving the plunger rod in a proximal direction will allow the plunger rod to move a short distance until the sharp-free ends 155 of the locking clip snap past the end of the plunger rod and engage inside surface 207 of the barrel sidewall. Further proximal motion of the plunger will be resisted by the locking element's engagement to the inside surface of the barrel sidewall. In addition, it is preferable to have a cam surface 242 on the stopper, positioned to contact the cantilevered leg locking element and force sharp-free ends 155 further into the syringe barrel wall as more proximally-directed force is used in an attempt to improperly reuse the syringe.

Figure 37:
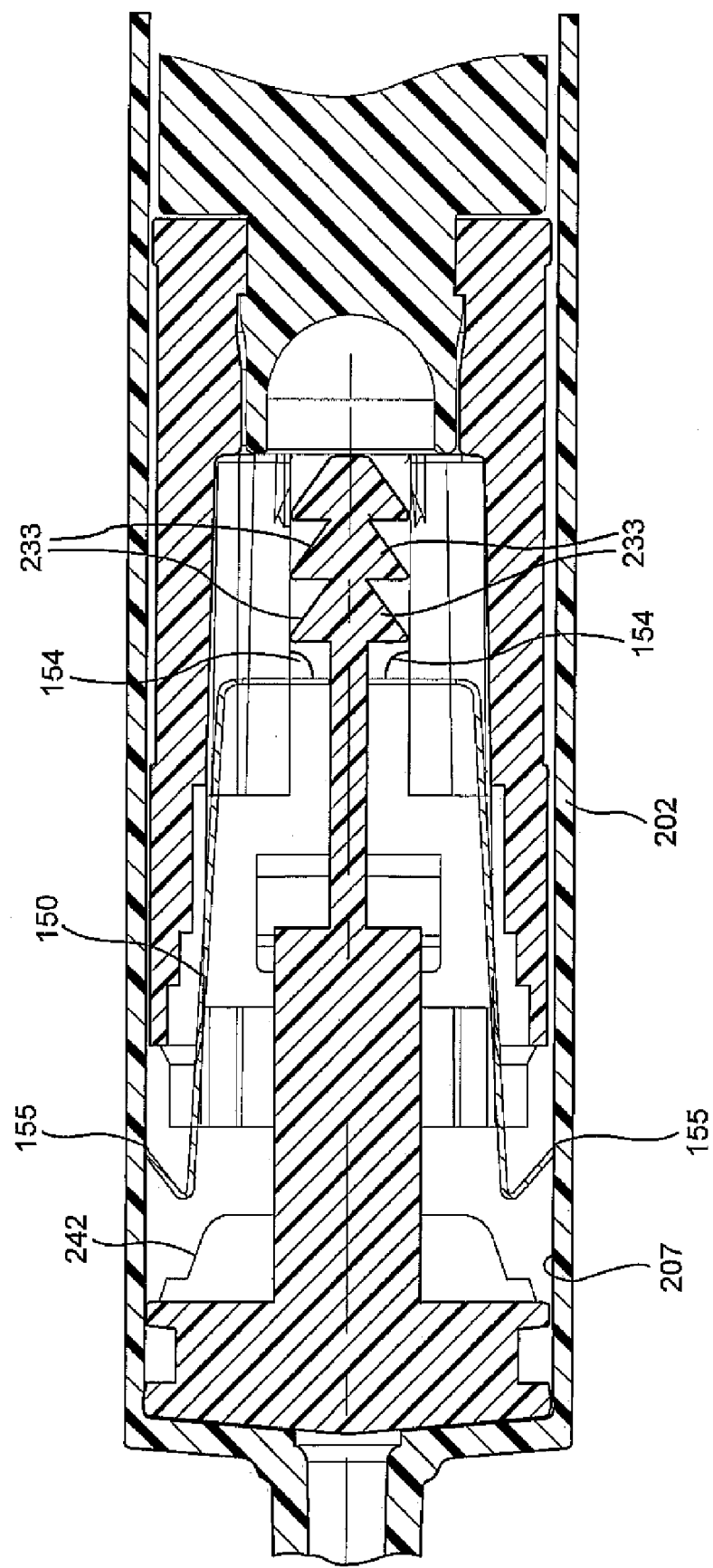
FIG. 37 is an enlarged partial cross-sectional view of the syringe assembly of FIG. 36 showing the interaction of internal components in the event of the use of even more, excessive, force in an attempt to withdraw the plunger rod.
Figure 38:
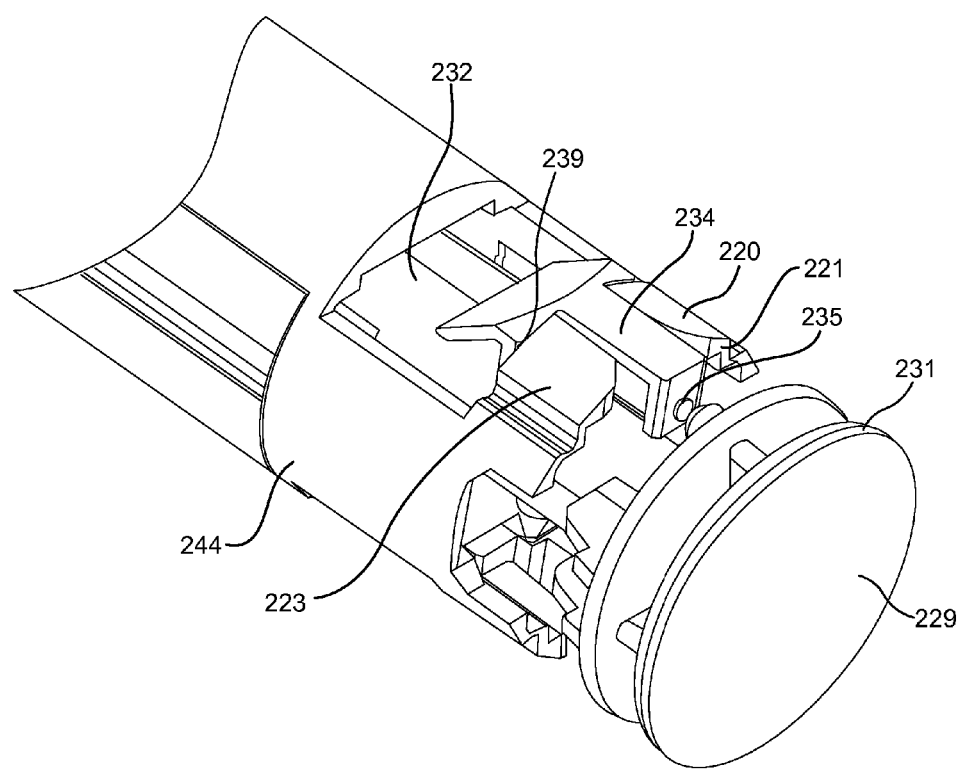
FIG. 38 is an enlarged partial perspective view similar to FIG. 37 but rotated 90°.

Further proximally-directed force, used in an attempt to improperly reuse the syringe assembly, will cause the proximal face of the positioning lug to transfer this excessive force to the proximal ledge of the retaining element of the stopper causing frangible connections 235 in the stopper to break separating the plunger rod and the stopper and destroying the functionality of the plunger assembly, as best illustrated in FIGS. 37 and 38. Accordingly, even if the excessive force on the plunger rod is strong enough to overpower the grip of the sharp-free end of the locking element on the inside surface of the barrel, the broken retaining elements facilitate the plunger rod leaving the syringe assembly without the stopper.

The plunger rod of the present invention is preferably a two-piece construction comprising a distal portion 244 and a proximal portion 245 connected so that the tangential force required to rotate the proximal portion of the plunger rod with respect to the distal portion is less than the axial force required to separate the proximal portion from the distal portion. In this embodiment the connection is provided by a distal projection 246 on proximal portion 245 of the plunger rod. The distal projection includes a raised peripheral protuberance 247. Distal portion 244 of the plunger rod includes a recess 251 for receiving distal projection 246. The recess is in proximal end 249 of the distal portion. A groove 253 is formed in the recess to accept raised peripheral protuberance 247 in a snap-fit arrangement. The protuberance is tapered distally inwardly to reduce engagement forces as the protuberance snaps into the groove while increasing disengagement forces. This is an important feature of the present embodiment because a user could attempt to properly reuse the syringe assembly by applying a tangential force or torque to rotate the proximal portion of the plunger in order to overpower the locking element and extract the plunger assembly from the barrel. In this structure the proximal portion of the plunger rod will rotate harmlessly rather than transferring the torque through the distal portion of the plunger rod. There are numerous ways to connect proximal and distal portions of the plunger rod so that connection is weaker in resisting rotation than in resisting tension. Structure being stronger in tension than in shear may be used, additional element between the proximal and distal portion of the plunger rod can be used to provide the desired properties. The intersection of the proximal and distal plungers can be held together by tightly wrapped film that is stronger in tension than in shear. All of these many ways to achieve a connection between the proximal and distal portions of the plunger rod which is weaker in torsion than in tension are within the purview of the present invention and the distal projection with a raised peripheral protuberance mating with a recess having a groove is merely representative of these many possibilities.

An important advantage of the present embodiment is that is resistant to excessive forces being applied to the barrel sidewall to disengage the structure which connects the plunger rod to the stopper. In the present embodiment excessive force on the plunger rod, even if capable of deflecting positioning lug 220 on the plunger rod, would only force the lug into deeper engagement with the stopper rather than disengagement. The embodiment of FIGS. 1-18 wherein outwardly extending rib 142 on cantilevered arm 140 could, arguably, be deflected out of the aperture 114 in the plunger rod by applying excessive force to the barrel sidewall, as with a tool, to force the outwardly extending rib in far enough to allow disengagement of the stopper in the plunger rod. The components of the embodiment of FIGS. 1-18 can be designed to minimize or eliminate this risk, however, the components of the present embodiment are inherently resistant to the manipulation of the plunger rod and the stopper by deflecting the barrel sidewall.

While various embodiments have been chosen to illustrate the invention, it will be appreciated that changes and modifications can be made without departing from the scope of the invention.

What is claimed is:

1. An operable syringe assembly having passive disabling structure comprising:
   a barrel including a cylindrical side wall having an inside surface defining a chamber for retaining fluid, an open proximal end and a distal end including a distal wall having a passageway therethrough in fluid communication with said chamber;
   an elongate plunger rod having a proximal end, an open distal end including a side wall having an interior surface, at least one detent on said interior surface, said side wall having an axial opening and a positioning lug projecting into said opening, said lug having a distal face and a proximal face;
   a stopper including a circular shaped sealing element having a peripheral surface forming a seal with said inside surface of said barrel, a boss member projecting proximally from said sealing element, at least one boss detent on said boss, a retaining element connected to said stopper by a frangible connection and defining an axial recess having a proximal ledge for accepting said positioning lug of said plunger and for limiting the axial motion of said positioning lug in said axial recess,
   a locking element including a central body portion having an aperture therethrough, at least one cantilevered leg extending distally outwardly from said body portion, and at least one finger element extending proximally inwardly from said aperture, said at least one leg having a sharp free end directed outwardly for engaging said inside surface of said barrel;
   said locking element being positioned with said sharp free end contacting said interior surface of said plunger rod proximally of said at least one detent, said boss member being positioned in said aperture of said locking element wherein said at least one finger element is contacting said boss proximally of said at least one boss detent, so that applying a proximally directed force to said plunger rod while holding said barrel causes said plunger rod to move proximally with respect to said stopper until said free end of said cantilevered leg moves distally along said inner surface of said plunger rod to said at least one detent and said proximal face of said positioning lug contacts said proximal ledge of said retaining element to move said stopper in a proximal direction for a selected distance, and subsequently applying a distally directed force to said plunger rod to discharge fluid from said chamber through said passageway causes said plunger rod to move in a distal direction along with said locking element due to its engagement with said at least one detent until said finger element of said locking element rides over said at least one boss detent and into contact with said at least one boss detent and said plunger rod contacts said stopper to move said stopper distally to discharge fluid from said chamber, after which applying a proximally directed force to said plunger rod will causes said plunger rod to move proximally until said free end of said cantilevered leg moves distally along said interior surface past said distal end of said plunger rod so that said sharp end of said at least one cantilever leg engages said inside surface of said barrel to help prevent proximal movement of said stopper to render said syringe assembly unusable.

2. The syringe assembly of claim 1 wherein said at least one detent in said plunger rod includes two axially spaced detents and said at least one detent on said boss includes two axially spaced boss detents so that said plunger rod can be moved distally two times before proximal motion of said plunger rod causes said locking element to engage said inside surface of said barrel.

3. The syringe assembly of claim 2 wherein said at least one cantilevered leg of said locking element includes two cantilevered legs positioned on opposite sides of said central body portion and two additional axially spaced detents are provided in said plunger rod opposite said two axially-spaced detents.

4. The syringe assembly of claim 3 further includes two radial projections on said stopper positioned to engage and force said two cantilevered legs outwardly when excessive proximally directed force is applied to said plunger rod in an attempt to overcome said locking element's engagement of said inside surface of said barrel.

5. The syringe assembly of claim 2 wherein said two axially spaced detents in said plunger rod include two axially spaced steps each having a blunt surface at its distal end extending inwardly from said interior surface.

6. The syringe assembly of claim 2 wherein said two axially spaced boss detents each include an inclined surface extending proximally inwardly and a blunt surface at a distal end of each of said inclined surfaces extending radially inwardly.

7. The syringe assembly of claim 1 including a flexible element connecting said positioning lug and said side wall of said plunger rod for allowing said positioning lug to flex outwardly during assembly with said stopper.

8. The syringe assembly of claim 7 wherein said positioning lug and said flexible element are integrally formed of thermoplastic material.

9. The syringe assembly of claim 7 wherein said retaining element of said stopper further includes a proximally and inwardly directed ramp surface for flexing said positioning element outwardly during assembly of said syringe assembly.

10. The syringe assembly of claim 1 wherein said axial opening includes two axial openings and said positioning lug includes at least one positioning lug projecting into each of said axial openings and said stopper includes an axial recess aligned with each of said axial openings.

11. The syringe assembly of claim 10 wherein each of said axial openings include at least two positioning lugs.

12. The syringe assembly of claim 1 wherein application of additional proximally directed force to the plunger rod after said sharp end of said at least one cantilevered leg engages said inside surface of said barrel will cause said proximal face of said positioning lug to contact said proximal ledge of said retaining element breaking said frangible connection with said stopper and releasing the stopper from engagement with said plunger rod.

13. The syringe assembly of claim 1 wherein said positioning lug includes at least two positioning lugs.

14. The syringe assembly of claim 1 wherein said plunger rod includes a distal portion and a proximal portion connected so that the tangential force required to rotate the proximal portion with respect to the distal portion is less than the axial force required to separate said proximal portion from said distal portion.

15. The syringe assembly of claim 1 wherein said distal wall of said barrel further includes an elongate tip extending distally therefrom having a passageway in fluid communication with said passageway in said distal wall.

16. The syringe of claim 1 further including a needle cannula having a distal end, a proximal end and a lumen therethrough, said proximal end of said needle cannula being connected to said distal end of said barrel so that said lumen is in fluid communication with said passageway.

17. The syringe assembly of claim 1 wherein said locking element is made of sheet metal.

18. The syringe assembly of claim 1 wherein said stopper is integrally formed of thermoplastic material.

* * * * *